US006805869B2

(12) United States Patent
Guo

(10) Patent No.: US 6,805,869 B2
(45) Date of Patent: Oct. 19, 2004

(54) CELLULAR VACCINES AND IMMUNOTHERAPEUTICS AND METHODS FOR THEIR PREPARATION

(75) Inventor: Yajun Guo, San Diego, CA (US)

(73) Assignee: Shanghai CP Guojian Pharmaceutical Co., Ltd., Shanghai (CN)

(*) Notice: Subject to any disclaimer, the term of this patent is extended or adjusted under 35 U.S.C. 154(b) by 0 days.

(21) Appl. No.: 09/216,604

(22) Filed: Dec. 17, 1998

(65) Prior Publication Data

US 2002/0102278 A1 Aug. 1, 2002

Related U.S. Application Data

(63) Continuation-in-part of application No. 08/872,527, filed on Jun. 11, 1997.
(60) Provisional application No. 60/019,639, filed on Jun. 12, 1996.

(51) Int. Cl.$^7$ ......................... A61K 45/00; A61K 47/00
(52) U.S. Cl. ............................. 424/278.1; 421/277.1; 435/455; 435/375; 435/383; 435/384; 435/386
(58) Field of Search ................................. 435/455, 375, 435/383, 384, 386; 424/277.1, 278.1

(56) References Cited

U.S. PATENT DOCUMENTS

| | | | |
|---|---|---|---|
| 4,605,011 A | | 8/1986 | Naslund |
| 4,697,600 A | | 10/1987 | Cardenas et al. |
| 4,844,893 A | | 7/1989 | Honsik et al. |
| 4,989,614 A | | 2/1991 | Dejter, Jr. et al. |
| 5,060,658 A | | 10/1991 | Dejter, Jr. et al. |
| 5,141,736 A | | 8/1992 | Iwasa et al. |
| 5,241,969 A | | 9/1993 | Carson et al. |
| 5,292,668 A | | 3/1994 | Paulus |
| 5,484,596 A | * | 1/1996 | Hanna, Jr. et al. |
| 5,530,101 A | | 6/1996 | Queen et al. |
| 5,582,996 A | | 12/1996 | Curtis |
| 5,591,828 A | | 1/1997 | Bosslet et al. |
| 5,601,819 A | | 2/1997 | Wong et al. |
| 5,635,600 A | | 6/1997 | Fanger et al. |
| 5,635,602 A | | 6/1997 | Cantor et al. |
| 5,637,481 A | | 6/1997 | Ledbetter et al. |
| 5,655,541 A | | 8/1997 | Vattuone |
| 5,669,394 A | | 9/1997 | Bergey et al. |
| 5,693,762 A | | 12/1997 | Queen et al. |
| 5,770,429 A | | 6/1998 | Lonberg et al. |
| 5,789,215 A | | 8/1998 | Berns et al. |
| 5,814,318 A | | 9/1998 | Lonberg et al. |

FOREIGN PATENT DOCUMENTS

| | | | |
|---|---|---|---|
| EP | 0 885 614 A2 | | 6/1998 |
| WO | WO 95/16775 | | 6/1995 |
| WO | WO 96/21673 | * | 7/1996 |
| WO | WO 98/24884 | | 6/1998 |

OTHER PUBLICATIONS

Guo et al. Nature Medicine, vol. 3(4), pp. 451–455, Apr. 1997.*
Shi et al. Proc. Amer. Assoc. Cancer Res. , vol. 37, p. 480, Abstract No. 3278, Mar. 1996.*
Guo et al. Science, vol. 263, pp. 518–520, 1994.*
Hogan et al. J. Exp. Med., vol. 168, pp. 725–736, 1988.*
Renner et al. Science, vol. 264, p. 833, 1994.*
Darlington et al . JNCL, vol. 64, p. 809, 1980.*
Chapoval et al. J. Immunol. vol. 155, pp. 1296–1303, 1995.*
Krummel et al. J. Exp. Med. vol. 182, pp. 459–465, 1995.*
Wang et al. Int. J. Cancer. vol. 51, pp. 962–967, 1992.*
Vanky et al. Semin. Cancer Biol. vol. 2(1, pp. 55–62, 1991.*
Janeway et al. Immuno Biology p. 7:10–7:12, 1994.*
Janeway et al. ImmunoBiology Appendix II and p. (2), 1994.*
Vaughan, Tristan J. et al., "Human antibodies by design," *Nature Biotechnology*, 16:535–539 (1998).
Reiter, Yoram et al., "Engineering antibody Fv fragments for cancer detection and therapy: Disulfide–stabilized Fv fragments," *Nature Biotechnology*, 14:1239–1245 (1996).
Guo, Ya–Jun et al., "Effective tumor vaccines generated by in vitro modification of tumor cells with cytokines and bispecific monoclonal antibodies," *Nature Medicine*, 4:451–455 (Apr., 1997).
Nestle, Frank O. et al, "Vaccination of melanoma patients with peptide– or tumor lysate–pulsed dendritic cells," *Nature Medicine*, 4:328–332 (1998).
Mayordomo, J. I. et al., "Bone marrow–derived dendritic cells pulsed with synthetic tumour peptides elicit protective and therapeutic antitumour immunity," *Nature Medicine*, 1:1297–1302 (1995).
Ostrand–Rosenberg, Suzanne, "Tumor immunotherapy: the tumor cell as an antigen–presenting cell," *Current Opinion in Immunology*, 6:722–727 (1994).
Panettieri, Jr., Reynold A. et al., "Activation of cAMP–Dependent Pathways in Human Airway Smooth Muscle Cells Inhibits TNF–α–Induced ICAM–1 and VCAM–1 Expression and T Lymphocyte Adhesion," *The Journal of Immunology*, 154:2358–2365 (1995).
Holliger, Philipp et al., "Antibodies come back from the brink," *Nature Biotechnology*, 16:1015–1016 (1998).

(List continued on next page.)

Primary Examiner—G. R. Ewoldt
(74) Attorney, Agent, or Firm—Morrison & Foerster LLP

(57) ABSTRACT

The present invention provides a method for enhancing the immunogenicity of weakly immunogenic or non-immunogenic cells, resulting in a cellular vaccine that can stimulate T cell activation, which in turn leads to an effective immune response. The cellular vaccines of the present invention are useful for the prevention and treatment of diseases which develop and/or persist by escaping the immune response triggered by T cell activation. Such diseases include, for example, all cancers, natural and induced immune deficiency states, and diseases caused by infections with a variety of pathogens.

8 Claims, 7 Drawing Sheets

OTHER PUBLICATIONS

Bubenik, J. et al., "Immunotherapy of cancer using local administration of lymphoid cells transformed by IL-2 cDNA and constitutively producing IL-2," *Immunology Letters*, 23:287–292 (1990).

Kubin, Marek et al., "Interleukin 12 Synergizes with B7/CD28 Interaction in Inducing Efficient Proliferation and Cytokine Production of Human T Cells," *J. Exp. Med.*, 180:211–222 (1994).

Li, Yiwen et al., "Costimulation by CD48 and B7-1 Induces Immunity against Poorly Immunogenic Tumors," *J. Exp. Med.*, 183:639–644 (1996).

Johnston, Janet V. et al., "B7–CD28 Costimulation Unveils the Hierarchy of Tumor Epitopes Recognized by Major Histocompatibility Complex Class 1–restricted CD8 Cytolytic T Lymphocytes," *J. Exp. Med.*, 183:791–800 (1996).

Haddada, H. et al., "Tumorigenicity of hamster and mouse cells transformed by adenovirus types 2 and 5 is not influenced by the level of class I major histocompatibility antigens expressed on the cells," *Proc. Natl. Acad. Sci. USA*, 83:9684–9688 (1986).

Gilliland, Lisa K. et al., "Universal bispecific antibody for targeting tumor cells for destruction by cytotoxic T cells," *Proc. Natl. Acad. Sci. USA*, 85:7719–7723 (1988).

Dranoff, Glenn et al., "Vaccination with irradiated tumor cells engineered to secrete murine granulocyte–macrophage colony–stimulating factor stimulates potent, specific, and long–lasting anti–tumor immunity," *Proc. Natl. Acad. Sci. USA*, 90:3539–3543 (1993).

Chen, Lieping et al., "Costimulation of Antitumor Immunity by the B7 Counterreceptor for the T Lymphocyte Molecules CD28 and CTLA–4," *Cell*, 71:1093–1102 (1992).

Baskar, Sivasubramanian et al., "Constitutive expression of B7 restores immunogenicity of tumor cells expressing truncated major histocompatibility complex class II molecules," *Proc. Natl. Acad. Sci. USA*, 90:5687–5690 (1993).

Armstrong, Todd D. et al., Major histocompatibility complex class II–transfected tumor cells present endogenous antigen and are potent inducers of tumor–specific immunity *Proc. Natl. Acad. Sci. USA*, 94:6886–6891 (1997).

Tsioulias, George J. et al., "Expression of HLA Class I Antigens in Sporadic Adenomas and Histologically Normal Mucosa of the Colon," *Cancer Research*, 53:2374–2378 (1993).

Johnstone, Alan et al., *Immunochemistry in Practice*, Chapter 2, pp. 30–47 (Blackwell, New York, 2d ed.) (1988).

Nabel, Gary J. et al., "Direct Gene Transfer for Treatment of Human Cancer," *Annals New York Academy of Sciences*, 772:227–231 (1995).

Allison, James P. et al., "Manipulation of costimulatory signals to enhance antitumor T–cell responses," *Current Opinion in Immunology.*, 7:682–686 (1995).

Jurianz, Katrin et al., "Adhesion function of Newcastle disease virus hemagglutinin in tumor–host interaction," *International Journal of Oncology*, 7:539–545 (1995).

Hock, Hanno et al., "Vaccinations with Tumor Cells Genetically Engineered to Produce Different Cytokines: Effectivity not Superior to a Classical Adjuvant," *Cancer Research*, 53:714–716 (1993).

Mattsson, Ragnar et al., "In Vivo Treatment with Interferon–Gamma during Early Pregnancy in Mice Induces Strong Expression of Major Histocompatibility Complex Class I and II Molecules in Uterus and Decidua But Not in Extra–Embryonic Tissues," *Biology of Reproduction*, 46:1176–1186 (1992).

Wang, Jianli et al., "Eliciting T Cell Immunity Against Poorly Immunogenic Tumors by Immunization with Dendritic Cell–Tumor Fusion Vaccines," *The Journal of Immunology*, 161:5516–5524 (1998).

Vaughan, Tristan J. et al., "Human Antibodies with Sub–nanomolar Affinities Isolated from a Large Non–immunized Phage Display Library," *Nature Biotechnology*, 14:309–314 (1996).

Asher, A. L. et al., "Murine Tumor Cells Transduced with the Gene for Tumor Necrosis Factor–α; Evidence for Paracrine Immune Effects of Tumor Necrosis Factor against Tumors," *The Journal of Immunology*, 146:3227–3234 (1991).

Yang, Guchen et al., "Antitumor Immunity Elicited by Tumor Cells Transfected with B7–2, a Second Ligand for CD28/CTLA–4 Costimulatory Molecules," *The Journal of Immunology*, 154:2794–2800 (1995).

Toffaletti, Dena L. et al., "Augmentation of Syngeneic Tumor–Specific Immunity by Semiallogeneic Cell Hybrids," *The Journal of Immunology*, 130:2982–2986 (1983).

Ostrand–Rosenberg, Suzanne et al., "Rejection of Mouse Sarcoma Cells After Transfection of MHC Class II Genes," *The Journal of Immunology*, 144:4068–4071 (1990).

MacLean, James A. et al., "Anti–CD3:Anti–IL–2 Receptor Bispecific Monoclonal Antibody," *The Journal of Immunology*, 150:1619–1628 (1993).

Blazar, Bruce R. et al., "In Vivo Blockade of CD28/CTLA4: B7/BB1 Interaction With CTLA4–Ig Reduces Lethal Murine Graft–Versus–Host Disease Across the Major Histocompatibility Complex Barrier in Mice," *Blood*, 83:3815–3825 (1994).

Gansbacher, Bernd et al., "Retroviral Vector–mediated γ–Interferon Gene Transfer into Tumor Cells Generates Potent and Long Lasting Antitumor Immunity," *Cancer Research*, 50:7820–7825 (1990).

Bakker, Alexander B. H. et al., "Generation of Antimelanoma Cytotoxic T Lymphocytes from Healthy Donors after Presentation of Melanoma–associated Antigen–derived Epitopes by Dendritic Cells in Vitro," *Cancer Research*, 55:5330–5334 (1995).

Ockert, Detlef et al.,"Newcastle Disease Virus–infected Intact Autologous Tumor Cell Vaccine for Adjuvant Active Specific Immunotherapy of Resected Colorectal Carcinoma," *Clinical Cancer Research*, 2:21–28 (1996).

Elliott, Bruce E. et al., "Perspectives on the Role of MHC Antigens in Normal and Malignant Cell Development," *Advances in Cancer Research*, 53:181–245 (1989).

Hellstrom, Karl Erik et al., "Can Co–stimulated Tumor Immunity be Therapeutically Efficacious?," *Immunological Reviews*, 145:123–145 (1995).

von Hoegen, Paul et al., "Modification of Tumor Cells by a Low Dose of Newcastle Disease Virus," *Cellular Immunology*, 126:80–90 (1990).

Linsley, Peter S. & Jeffrey A. Ledbetter, "The Role of the CD28 Receptor During T Cell Responses to Antigen," *Annu. Rev. Immunol.*, 11:191–212 (1993).

Hock, Hanno et al., "Interleukin 7 Induces CD4+ T Cell–dependent Tumor Rejection," *J. Exp. Med.*, 174:1291–1298 (1991).

Colombo, Mario P. et al., "Granulocyte Colony–stimulating Factor Gene Transfer Suppresses Tumorigenicity of a Murine Adenocarcinoma In Vivo," *J. Exp. Med.*, 173:889–897 (1991).

Donnelly, John J. et al., "Immunization with DNA," *Journal of Immunological Methods*, 176:145–152 (1994).

Young, James W. et al., "Dendritic Cells as Adjuvants for Class I Major Histocompatibility Complex–restricted Antitumor Immunity," *J. Exp. Med.*, 183:7–11 (1996).

Zitvogel, Laurence et al., "Therapy of Murine Tumors with Tumor Peptide–pulsed Dendritic Cells: Dependence on T Cells, B7 Constimulation, and T Helper Cell 1–associated Cytokines," *J Exp. Med.*, 183:87–97 (1996).

Celluzzi, Christina M. et al., "Peptide–pulsed Dendritic Cells Induce Antigen–specific, CTL–mediated Protective Tumor Immunity," *J. Exp. Med.*, 183:283–287 (1996).

Caux, Christophe et al., "B70/B7–2 Is Identical to CD86 and Is the Major Functional Ligand for CD28 Expressed on Human Dendritic Cells," *J. Exp. Med.*, 180:1841–1847 (1994).

Hurtado, José C. et al., "Potential Role of 4–IBB in T Cell Activation; Comparison with the Costimulatory Molecule CD28," *The Journal of Immunology*, 155:3360–3367 (1995).

Porgador, Angel et al., "Interleukin 6 Gene Transfection into Lewis Lung Carcinoma Tumor Cells Suppresses the Malignant Phenotype and Confers Immunotherapeutic Competence against Parental Metastatic Cells," *Cancer Research*, 52:3679–3686 (1992).

Reeves, Mark E. et al., "Retroviral Transduction of Human Dendritic Cells with a Tumor–associated Antigen Gene," *Cancer Research*, 56:5672–5677 (1996).

Luboldt, Hans–Joachim et al., "Selective Loss of Human Leukocyte Antigen Class I Allele Expression in Advanced Renal Cell Carcinoma," *Cancer Research*, 56:826–830 (1996).

Bode, Christoph et al., "Antibody–directed Fibrinolysis," *The Journal of Biological Chemistry*, 264:944–948 (1989).

Hathcock, Karen S. et al., "Identification of an Alternative CTLA–4 Ligand Costimulatory for T Cell Activation," *Science*, 262:905–907 (1993).

Guo, Yajun et al., "Effective Tumor Vaccine Generated by Fusion of Hepatoma Cells with Activated B Cells," *Science*, 263:518–520 (1994).

Townsend, Sarah E. & James P. Allison, "Tumor Rejection After Direct Costimulation of CD8+ T Cells by B7–Transfected Melanoma Cells," *Science*, 259:368–370 (1993).

Leach, Dana R. et al., "Enhancement of Antitumor Immunity by CTLA–4 Blockade," *Science*, 271:1734–1736 (1996).

Trojan, Jerzy et al., "Treatment and Prevention of Rat Glioblastoma by Immunogenic C6 Cells Expressing Antisense Insulin–Like Growth Factor I RNA," *Science*, 259:94–96 (1993).

Renner, Christoph et al., "Cure of Xenografted Human Tumors by Bispecific Monoclonal Antibodies and Human T Cells," *Science*, 264:833–835 (1994).

Allison, James P. & Matthew F. Krummel, "The Yin and Yang of T Cell Costimulation," *Science*, 270:932–933 (1995).

Chang et al., *Gastroenterology*, 112(4):A546 (1997).

Ikeda, Mitsunori et al., "Suppressive Effect of Antioxidants on Intercellular Adhesion Molecule–1 (ICAM–1) Expression in Human Epidermal Keratinocytes," *J. Invest. Dermatol.*, 103:791–796 (1994).

Hoogenboom, Hennie R. et al., "Antibody phage display technology and its applications," *Immunotechnology*, 4:1–20 (1998).

Golumbek, Paul T. et al., "Treatment of Established Renal Cancer by Tumor Cells Engineered to Secrete Interleukin–4," *Science*, 254:713–716 (1991).

Freeman, Gordon J. et al., "Cloning of B7–2: A CTLA–4 Counter–Receptor That Costimulates Human T Cell Proliferation," *Science*, 262:909–911 (1993).

Wallich, R. et al., "Abrogation of metastatic properties of tumour cells by de novo expression of H–2K antigens following H–2 gene trasfection," *Nature*, 315:301–315 (1985).

Shahinian, Arda et al., "Differential T Cell Costimulatory Requirements in CD28–Deficient Mice," *Science*, 261:609–612 (1993).

Murphy, Erin E. et al., "B7 and Interleukin 12 Cooperate for Proliferation and Interferon γ Production by Mouse T Helper Clones That Are Unresponsive to B7 Costimulation," *J. Exp. Med.*, 180:223–231 (1994).

Paglia, Paola et al., "Murine Dendritic Cells Loaded In Vitro with Soluble Protein Prime Cytotoxic T Lymphocytes against Tumor Antigen In Vivo," *J. Exp. Med.*, 183:317–322 (1996).

Luster, Andrew D. et al., "IP–10, a –C–X–C– Chernokine, Elicits a Potent Thymus–dependent Antitumor Response In Vivo," *J. Exp. Med.*, 178:1057–1065 (1993).

Porgador, Angel et al., "Bone Marrow–generated Dendritic Cells Pulsed with a Class I–restricted Peptide Are Potent Inducers of Cytotoxice T Lymphocytes," *J. Exp. Med.*, 182:255–260 (1995).

Seder, Robert A. et al., "CD28–mediated Costimulation of Interleukin 2 (IL–2) Production Plays a Critical Role in T Cell Priming for IL–4 and Interferon γ Production," *The Journal of Experimental Medicine*, 179:299–304 (1994).

Gong, Jianlin et al., "Induction of antitumor activity by immunization with fusions of dendritic and carcinoma cells," *Nature Medicine*, 3(5):558–561 (1997).

Melero, Ignacio et al., "Monoclonal antibodies against the 4–1BB T–cell activation molecule eradicate established tumors," *Nature Medicine*, 3:682–685 (1997).

Hsu, Frank J. et al., "Vaccination of patients with B–cell lymphoma using autologous antigen–pulsed dendritic cells," *Nature Medicine*, 2(1):52–58 (1996).

Linsley, Peter S. et al., "CTLA–4 Is a Second Receptor for the B Cell Activation Antigen B7," *J. Exp. Med.*, 174:561–569 (1991).

DeBenedette, Mark A. et al., "Role of 4–1BB Ligand in Costimulation of T Lymphocyte Growth and its Upregulation on M12 B Lymphomas by cAMP," *J. Exp. Med.*, 181:985–992 (1995).

June, Carl H. et al., "The B7 and CD28 receptor families," *Immunology Today*, 15:321–331 (1994).

Boczkowski, David et al., "Dendritic Cells Pulsed with RNA are Potent Antigen–presenting Cells In Vitro and In Vivo," *J. Exp. Med.*, 184:465–472 (1996).

Tykocinski, Mark L. et al., "Antigen–Presenting Cell Engineering," *American Journal of Pathology*, 148:1–16 (1996).

Ulevitch, Richard J. et al., "Hyperexpression of Interferon–gamma–induced MHC Class II Genes Associated with Reorganization of the Cytoskeleton," *American Journal of Pathology*, 139:287–296 (1991).

Saito, Ichiro et al., "Expression of Cell Adhesion Molecules in the Salivary and Lacrimal Glands of Sjogren's Syndrome," *Journal of Clinical Laboratory Analysis*, 7:180–187 (1993).

Zöller et al., "Interleukin–1 Production by Transformed Fibroblasts. II. Influence on Antigen Presentation and T–Cell–Mediated Anti–Tumor Response," *Intl. J. Cancer*, 50:450–457 (1992).

Darlington, Gretchen J. et al., "Expression of Liver Phenotypes in Cultured Mouse Hepatoma Cells," *Journal of the National Cancer Institute*, 64:809–815 (1980).

Restifo, Nicholas P. et al., "Molecular Mechanisms Used by Tumors to Escape Immune Recognition: Immunogenetherapy and the Cell Biology of Major Histocompatibility Complex Class I," *Journal of Immunotherapy*, 14:182–190 (1993).

Holliger, Philipp et al., "Retargeting serum immunoglobulin with bispecific diabodies," *Nature Biotechnology*, 15:632–636 (1997).

Merchant, A. Margaret et al., "An efficient route to human bispecific IgG," *Nature Biotechnology*, 16:677–681 (1998).

McGuinness, Brian T. et al., "Phage diabody repertoires for selection of large numbers of bispecific antibody fragments," *Nature Biotechnology*, 14:1149–1154 (1996).

Liu, Margaret, "Transfected human dendritic cells as cancer vaccines," *Nature Biotechnology*, 16:335–336 (1998).

Tepper, Robert I. et al., "Murine Interleukin–4 Displays Potent Anti–Tumor Activity In Vivo," *Cell*, 57:503–512 (1989).

Fearon, Eric R. et al., "Interleukin–2 Production by Tumor Cells Bypasses T Helper Function in the Generation of an Antitumor Response," *Cell*, 60:397–403 (1990).

Ertel, Christian et al., "Viral hemagglutinin augments peptide–specific cytotoxic T cell responses," *Eur. J. Immunol.*, 23:2592–2596 (1993).

Willems, Fabienne et al., "Interleukin–10 inhibits B7 and intercellular adhesion molecule–1 expression on human monocytes," *Eur. J. Immunol.*, 24:1007–1009 (1994).

Alderson, Mark R. et al., "Molecular and biological characterization of human 4–1BB and its ligand," *Eur. J. Immunol.*, 24:2219–2227 (1994).

Green, Jonathan M. et al., "Absence of B7–Dependent Responses in CD28–Deficient Mice," *Immunity*, 1:501–508 (1994).

*Molecular Biology of the Cell*, pp. 47–58 & pp. 276–337, Second Edition, published by Garland Publishing, Inc., NY & London.

\* cited by examiner

CELLULAR VACCINES AND IMMUNOTHERAPEUTICS AND METHODS FOR THEIR PREPARATION

RELATED APPLICATIONS

The present application is a continuation-in-part of application Ser. No. 08/872,527, filed Jun. 11, 1997, which claims the priority benefit of U.S. provisional application 60/019,639, filed Jun. 12, 1996, all of which are incorporated by reference herein.

FIELD OF THE INVENTION

The present invention provides a method for enhancing the immunogenicity of weakly immunogenic or non-immunogenic cells in order to provide the immune system with an immunogenic signal capable of stimulating T cell activation leading to an effective immune response. The method of the invention generates cellular vaccines which are useful for the prevention and treatment of diseases which develop and/or persist by escaping the immune response triggered by T cell activation. Such diseases include, for example, all cancers, natural and induced immune-deficiency states, and diseases caused by infections with a variety of pathogens.

BACKGROUND OF THE INVENTION

U.S. Pat. No. 5,484,596 by Hanna et al. describes using tumor tissue as a vaccine. U.S. Pat. No. 4,844,893 by Honsik et al. describes arming IL-2-activated leukocytes with Mabs directed to antigens preferentially expressed on tumor cells for killing the target cells. Both patents are incorporated by reference herein.

Anti-tumor immune responses are mediated primarily by T lymphocytes. Down regulation of both the major histocompatibility complex (MHC) and the molecules that costimulate the immune response is associated with defective T cells activation signaling by tumor cells (Luboldt et al., Cancer Res. 56:826–830, 1996; L. Chen et al., 1992, Cell 1: 1093; P. S. Linsley, J. A. Ledbetter, 1993, Ann. Rev. Immunol 11: 191; G. J. Freeman et al., 1993, Science 262: 909; C. H. June et al., 1994, Immune. Today 15: 321; J. T. Gerge et al., 1993, Cancer Res. 53: 2374; Ostrand-Rosenberg, 1993, S. Curr. Opin. Immune. 6: 772; B. E. Elliot et al., 1989, Adv. Cancer Res. 53: 181).

T cell receptor (TCR) recognition of MHC-bound antigen is not a sufficient signal for T cell activation. Costimualtory molecules, such as B7-1 and B7-2, are cell surface proteins of antigen presenting cells (APCs), and other cells targeted by the immune response, that provide critical signals for T cell activation (for review, see L. Chen et al., 1995, Immunol. Rev. 145: 123; T. Tykocinski et al., 1996, Am. J. Path. 148: 1). B7 signaling via the T cell surface molecule CD28 appears to be the major costimulatory pathway for T cell activation. However, recent studies show that costimulation is a more complex event which involves both cytokines and adhesion molecules (G. Yang et al., 1995, J. Immune. 154: 2794; M. Kubin et al., 1994, J. Exp. Med. 180: 211; Y. Li et al., 1996, J. Exp. Med. 183: 639).

Many approaches have been used to enhance the immunogenicity of tumor cells (see, for example, the references cited in this section). The major approaches presently under investigation involve gene transfer. In this regard, most of the methods employed to date have required ex vivo or in vivo transfection with genes such as MHC or B7, or modification of tumor cells with antigen presenting cells (APCs) (Y. J. Guo et al., 1994, Science 263: 518; M. Tykocinski, 1996, A. J. Path. 148: 1; J. Young and K. Inaba, 1996, J. Exp. Med. 183: 7; L. Zitvogel et al., 1996, J. Exp. Med. 183: 87; C. M. Celluzzi et al., 1996, J. Exp. Med. 183: 283). These approaches are time consuming and problematic because of the poor transfectability of primary tumor cells and because of the requirement for large numbers of APCs.

In vitro treatment of tumor cells with cytokines increases the expression of MHC and adhesion molecules (R. Mattsson et al., 1992, Biol-Reprod 46: 1176; R. J. Ulevitch et al., 1991, Am. J. Pathol. 139: 287; F. Willems et al., 1994, Eur. J. Immune. 24: 1007; I. Saito et al., 1993, J. Clin. Lab. Anal. 7: 180; R. A. Panettieri et al., 1994, J. Immune. 154: 1358; M. Ikeda et al., 1994, J. Invest. Dermatol. 103: 791). Transfection of tumor cells with MHC, B7-1 and B7-2 genes converts low immunogenic tumor cell lines to immunogenic cell lines (S. E. Townsend and J. P. Allison, Science 259: 368; J. P. Allison et al., 1995, Curr. Opin. Immune. 7: 682; G. Yang et al., 1995, J. Immune. 154: 2794; M. Kubin et al., 1994, J. Exp. Med. 180: 211). Non-immunogenic tumor cells are not responsive to transfection with the B7 gene alone but can become responsive by co-expression of CD48 molecules at the cell surface (Y. Li et al., 1996, J. Exp. Med. 183: 639).

The costimulatory molecule B7 can under some circumstances deliver a negative signal through its binding to CTLA-4, a second receptor for B7 on T cells. Cross-linking CTLA-4 molecules in vitro has been shown to inhibit T cell proliferation. Furthermore, mice deficient in CTLA-4 develop severe T cell proliferative disorders (K. Kawai et al., 1993, Science 261: 609; J. P. Allison, M. K. Krummel, 1995, Science 270: 932; J. M. Green et al., 1994, Immunity 1: 501). A recent report showed that the introduction of anti-CTLA-4 monoclonal antibody (MAb), which blocks CTLA-4 mediated signaling, resulted in enhanced T cell-dependent rejection of tumors in certain mouse models (D. R. Leach et al., 1996, Science 271: 1734). These data provide evidence that CTLA-4 may be counter-regulatory to the CD28 costimulatory signal. Thus, transfected tumor cells expressing B7 molecules may fail to elicit effective immunity due to CTLA-4 mediated negative signaling.

In addition to T cell activation using B7 gene transfection, bispecific monoclonal antibodies (Bi-MAbs) in combination with pre-stimulated lymphocytes have been used to induce T cell activation under certain circumstances. For example, one study reports that costimulatory signals can be delivered by a combination of Bi-MAbs to CD28:CD30 (CD30 is a Hodgkin's tumor-associated antigen) and CD3:CD30 in combination with peripheral blood lymphocytes (PBLs) pre-stimulated with the CD3:CD30 Bi-MAb in the presence of CD30$^+$ Hodgkin's tumor-derived cells; however, the combination of CD28:CD30 and CD3:CD30 Bi-MAbs alone did not induce significant in vitro cytotoxicity of resting human PBLs against a Hodgkin's tumor-derived cell line, and stimulation with the CD28:CD30 Bi-MAb alone was not effective (C. Renner et al., 1994, Science 264: 833). Similarly, regression of Hodgkin's derived tumor xenografts was observed only when both the CD28:CD30 and CD3:CD30 Bi-MAbs were used in combination with PBLs prestimulated in vitro with CD30$^+$ cells and CD3:CD30 Bi-MAb; no significant effect was observed in xenografts treated with either of the Bi-MAbs alone, or a combination of the two Bi-MAbs without prestimulated human PBLs (Renner et al., supra).

SUMMARY OF THE INVENTION

The present invention features immunogenic tumor cells and other immunogenic autologous cells, convenient methods of making such immunogenic cells, methods of using such immunogenic cells to activate or enhance immune response against diseased cells with minimum effect on normal or healthy cells, and methods of avoiding the negative T cell signaling pathway.

The present invention provides a method for enhancing the immunogenicity of weakly-immunogenic or non-immunogenic cells, resulting in a cellular vaccine that can stimulate T cell activation, which in turn leads to an effective immune response against diseased cells. The cellular vaccines of the present invention can be used as vaccines to prevent diseases and as immunotherapeutics to treat diseases. The starting materials for the cellular vaccine can be a target diseased cell (e.g., autologous or in vivo diseased cells and in vitro transformed cell lines), or an antigen presenting cell presenting one or more antigens associated with a disease (e.g., dendritic cells, macrophages, B cells, and other cells fused with diseased cell, pulsed with antigens or transfected with antigen expressing nucleic acid).

In summary, the method of the invention involves the steps of (1) treating weakly- or non-immunogenic autologous cells (target cells) in order to amplify primary and costimulatory T cell activation signals in the cells, and (2) attaching to the treated cells a substance capable of binding to one or more antigens on the treated cells and to one or more T cell activation costimulatory molecules on the surface of T cells (such as CD28), thereby providing the treated cells with the capacity to physically link to T cells and to activate the costimulatory signal. Such substances include, but are not limited to, bispecific monoclonal antibodies (Bi-MAbs) targeted to antigen on the treated cells and to CD28 and/or other costimulatory molecules on T cells. The first step may be skipped when the autologous cell is attached with (1) a bridge molecule with two or more binding sites for T cell activation costimulatory molecules on the surface of T cells, or (2) two or more bridge molecules each with one or more binding sites for T cell activation costimulatory molecules on the surface of T cells. The fist step may also be skipped when the target cells are antigen presenting cells presenting one or more antigens associated with a disease.

Once the primary and/or costimulatory T cell activation signals in the target diseased cells have been amplified by cytokines or other means and the bridge molecules have been attached to the target diseased cells, the cytokines and the bridge molecules not attached to the target diseased cells may be removed from the immunogenic composition before the target diseased cells are administered to a patient. This additional step minimizes adverse effects associated with administering cytokines to a patient. It also minimizes the risk associated with allowing bridge molecules not attached to a target diseased cell into a patient, an event which may cause unwanted immune response against normal or healthy cells.

The first step of the method up-regulates antigen processing capacity within the treated cells and amplifies the expression of cell surface molecules involved in T cell activation. The second step provides the treated cells with a means to physically bridge to T cells via CD28 and/or other costimulatory molecules, thereby providing optimal conditions for stimulating T cell activation.

Thus, in a first aspect, this invention features an immunogenic composition for administration to a patient mammal (including a human) having target diseased cells. The immunogenic composition contains an autologous target diseased cell which differs from the diseased cells in the patient in that it processes and presents antigens characteristic of the diseased cells more effectively. For example, the autologous target diseased cell expresses one or more primary (e.g., MHC) and/or costimulatory (e.g., B7-1 and B7-2) T cell activation molecules at a higher level (e.g., 50% higher, preferably 2 folds higher, more preferably 10 folds higher). As described below, there are different ways of enhancing the expression level of the primary and/or costimulatory T cell activation molecules.

In addition, the autologous target diseased cell has attached thereto one or more bridge molecules. Each bridge molecule has one or more binding sites for one or more costimulatory molecules on the surface of effector cells, which include, but are not limited to, T cells, NK cells, macrophages, LAK cells, B cells, and other white blood cells. Preferably, though not required, the bridge molecules have one or more binding sites for one or more antigens on the surface of the target diseased cell and are attached to the target diseased cells at the cell surface antigens. In another preferred embodiment, substantially all (e.g., >80%, preferably >90%, more preferably >95%) the bridge molecules in the immunogenic composition are attached to the autologous target diseased cells so that the composition is substantially free of bridge molecules not attached to a target diseased cell. In a further preferred embodiment, the immunogenic composition contains a pharmaceutically effective amount of the target diseased cells with bridge molecules attached thereto.

By "immunogenic" is meant the ability to activate the response of the whole or part of the immune system of a mammal, especially the response of T cells.

By "autologous" is meant that the target diseased cell is from the patient mammal, or from another patient having a common major histocompatibility phenotype. An autologous target cell may be obtained from the patient mammal or another source sharing the same MHC with methods known to those skilled in the art. Once taken from a patient, an autologous cell may be modified, transfected, and treated by methods described herein.

By "target diseased cell" is meant a cell causing, propagating, aggravating or contributing to a disease in a patient mammal. Target diseased cells include, but are not limited to, tumor cells (including unmodified tumor cells, tumor cells modified with different approaches, and primary culture). The sources of tumor cells include, but are not limited to, liver cancer, hepatocellular carcinoma, lung cancer, gastric cancer, colorectal carcinoma, renal carcinoma, head and neck cancers, sarcoma, lymphoma, leukemia, brain tumors, osterosarcoma, bladder carcinoma, myloma, melanoma, breast cancer, prostate cancer, ovarian cancer, and pancreas carcinoma.

Target diseased cells may also be cells infected with prions (which cause Mad Cow diseases among others), viruses, bacteria, fungi, protozoa or other parasites (e.g. worms).

Viruses include those described or referred to in *Fields Virology Second Edition,* 1990, Raven Press, New York, incorporated by reference herein. Examples include, but are not limited to, herpes virus, rhinoviruses, hepatitis virus (type A, B, C and D), HIV, EBV, HPV, and HLV.

Bacteria include those described or referred to in *Bergey's Manual of Determinative Bacteriology Ninth Edition,* 1994, Williams and Wilkins, incorporated by reference herein. Examples include, but are not limited to, gram positive and negative bacteria, *streptococci, pseudomonas* and *enterococci, Mycobacterium tuberculosis, Aeromonas* hydrophilia, Aeromonas caviae, Aeromonas sobria, Streptococcus uberis, Enterococcus faecium, Enterococcus faecalis, Bacillus sphaericus, Pseudomonas fluorescens, Pseudomonas putida, Serratia liquefaciens, Lactococcus lactis, Xanthomonas maltophilia, Staphylococcus simulans, Staphylococcus hominis, Streptococcus constellatus, Streptococcus anginosus, Escherichia coli, Staphylococcus aureus, Mycobacterium fortuitum, and Klebsiella pneumonia.

Primary T cell activation molecules include MHC class I, MHC class II and other molecules associated with antigen processing and/or presentation. Costimulatory T cell activation molecules include ICAM-1, ICAM-2, ICAM-3, LFA-1, LFA-2, VLA-1, VCAM-1, 4–1-BB, B7-1, B7-2, and other cell adhesion proteins and other cell surface proteins which can activate T cell costimulatory pathways through T cell surface proteins.

By "bridge molecule" is meant a molecule or substance which can bring two or more cells together by attaching to the cells with its binding sites. Preferably, a bridge molecule can bring an autologous target diseased cell together with an effector cell and deliver a signal to the effector cell to activate or enhance the effector cell's immune response against the target. A bridge molecule has one or more binding sites for stimulatory and/or costimulatory molecules on the effector cells. These binding sites can be designed to activate a positive regulator of T cell activation (e.g., CD28, 4–1BB) but avoid stimulating a negative regulator of T cell activation (e.g., CTLA-4). The binding sites can also be designed to blockade a negative regulator of T cell activation (see Leach et al., Science 271:1734–1736, 1996). A bridge molecule may also have one or more binding sites for antigens on the surface of the target diseased cell. Bridge molecules include, but are not limited to, bispecific monoclonal antibodies, fusion proteins, organic polymers, and hybrids of chemical and biochemical materials. The antibodies described or disclosed in U.S. Pat. Nos. 5,601,819, 5,637,481, 5,635,602, 5,635,600, 5,591,828, 5,292,668 and 5,582,996 are incorporated by reference herein.

The antigen on the target cell serving as an anchor for the bridge molecule need not be unique to the target cell when the bridge molecule is attached to the target cell in vitro. Any molecule on the target cell surface can be used to anchor the bridge molecule, including, but not limited to, proteins, glycoproteins, lipids, glycolipids, phospholipids, lipid aggregates, steroids, and carbohydrate groups such as disaccharides, oligosaccharides and polysaccharides (see "Molecular Biology of The Cell," pp47–58, pp276–337, Second Edition, published by Garland Publishing, Inc. NY & London). Examples include transferrin receptor, Low Density Lipoprotein (LDL) receptor, gp55, gp95, gpl 15, gp210, CD44, ICAM-1, ICAM-2, collagen and fibronectin receptor, transferrin receptors, Fc receptor, and cytokine receptors.

Costimulatory molecules on the surface of effector cells may be antigens, fatty acids, lipids, steroids and sugars that can stimulate or costimulate these effector cells' functions to destroy the target cells. Costimulatory molecules include, but are not limited to, CD1 a, CD1b, CD1c, CD2, CD2R, CD3, CD4, CD5, CD6, CD7, CD8, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD45RA, CD45RB, CD45RO, CD46, CD47, CD48, CD49a, CD49b, CD49c, CD49d, CD49e, CD49f, CD50, CD51, CD51/61 complex, CD52, CD53, CD54, CD55, CD56, CD57, CD58, CD59, CDw60, CD61, CD62E, CD62L, CD62P, CD63, CD64, CDw65, CD66a, CD66b, CD66c, CD66d, CD66e, CD67, CD68, CD69, CD70, CD71, CD72, CD73, CD74, CDw75, CDw76, CD77, CDw78, CD79a, CD80, CD81, CD82, CD83, CDw84, CD85, CD86, CD87, CD88, CD89, CDw90, CD91, CDw92, CD93, CD94, CD95, CD96, CD97, CD98, CD99, CD99R, CD100, CDw101, CD102, CD103, CD104, CD105, CD106, CD107a, CD107b, CDw108, CDw109, CD110–CD114, CD115, CDw116, CD117, CD118*, CD119, CD120a, CD120b, CDw121a, CDw121b, CD122, CD123*, CDw124, CD125*, CD126, CDw127, CDw128, CD129, CDw130, LFA-1, LFA-2, LFA-3, VLA-1, VCAM-1, VCAM-2, 4–1BB, cytokine and chemokin receptors. In a preferred embodiment, the bridge molecule has a binding site for CD28 or 4-1BB on the surface of T cells.

By "pharmaceutically effective" is meant the ability to cure, reduce or prevent one or more clinical symptoms caused by or associated with the diseased cells in the patient mammal, including, but not limited to, uncontrolled cell proliferation, bacteria infection, and virus infection.

The immunogenic composition may be isolated, enriched or purified for administration to a patient.

By "isolated" in reference to the immunogenic composition is meant that the autologous target diseased cell is isolated from a natural source. Use of the term "isolated" indicates that one or more naturally occurring materials have been removed from the normal environment. Thus, the target diseased cell may be placed in a different cellular environment or in a solution free of other cells. The term does not imply that the target diseased cell is the only cell present, but does indicate that it is the predominate cell present (at least 20–50% more than any other cells) and is essentially free (about 90% pure at least) of other tissues naturally associated with it in the body of the patient. In a preferred embodiment, the composition is substantially free of effector cells such as T cells. In another preferred embodiment, the composition is substantially free of bridge molecules not attached to a target diseased cell. In a third preferred embodiment, the composition is substantially free of cytokines outside of the target diseased cell.

By "enriched" in reference to the immunogenic composition is meant that the autologous target diseased cell constitutes a significantly higher fraction (2–5 fold) of the total cells in the composition than in the diseased tissue in the patient's body. This could be caused by a person by preferential reduction in the amount of other cells present, or by a preferential increase in the amount of the specific target diseased cells, or by a combination of the two. However, it should be noted that enriched does not imply that there are no other cells present, just that the relative amount of the cell of interest has been significantly increased in a useful manner. The term "significantly" here is used to indicate that the level of increase is useful to the person making such an increase, and generally means an increase relative to other cells of about at least 2 fold, more preferably at least 5 to 10 fold or even more.

By "purified" in reference to the immunogenic composition does not require absolute purity (such as a homogeneous preparation); instead, it represents an indication that the target diseased cell is relatively purer than in the natural environment. The target diseased cells could be obtained directly from the patient or from cell culture, with or without modifications. Purification of at least one order of magnitude, preferably two or three orders, and more preferably four or five orders of magnitude is expressly contemplated. In a preferred embodiment, the composition is substantially free of effector cells such as T cells.

The immunogenic composition may contain a pharmaceutically suitable carrier or excipient. Techniques for formulation and administration may be found in *Remington's Pharmaceutical Sciences,* 18th ed., Mack Publishing Co., Easton, Pa. (1990). The immunogenic composition may be administered to a patient systemically, e.g., by intravenous infusion or subcutaneous injection. A composition of the invention may be administered as a unit dose to a patient mammal, each unit containing a predetermined quantity (e.g., about $1\times10^5$ to about $1\times10^{10}$, preferably about $1\times10^6$ to about $1\times10^9$, and more preferably about $1\times10^7$ to about $1\times10^8$) of armed and/or activated autologous target diseased cells calculated to produce the desired therapeutic effect in association with the physiologically tolerable aqueous medium as diluent.

The expression of primary and costimulatory T cell activation molecules may be enhanced by various means, for example, in vitro, ex vivo or in vivo treatment of target cells with cytokines or other factors capable of inducing the desired amplification; and in vitro and in vivo transfer to the target cells of MHC genes, adhesion molecule genes, cytokine genes, and/or their respective transcription activators or enhancers. Cytokines include those described or referred to in *The Cytokine Handbook*, Thomson, A., (ed.), 1994, Academic Press, San Diego, incorporated by reference herein. Examples include, but are not limited to, IL-1, IL-2, IL-3, IL-4, IL-5, IL-6, IL-7, IL-8, IL-9, IL-10, IL-11, IL-12, IL-13, IL-14, IL-15, IL-16, IL-17, G-CSF, GM-CSF, inteferons (e.g., IFN $\alpha$, $\beta$, and $\gamma$), tumor necrosis factors (e.g., INF$\alpha$, and $\beta$) and other chemokines and lymphokines. In a preferred embodiment, IFN$\gamma$ and TNF$\alpha$ are used either alone or in combination to enhance the expression of primary and costimulatory T cell activation molecules in autologous target diseased cells.

The bridge molecule may be attached to the target cells by various means, for example, in vitro, ex vivo or in vivo treatment of target cells with the bridge molecule. When a target diseased cell coated with bridge molecules is administered into a patient, it will bind to costimulatory molecules on the surface of the effector cells. The more densely the target diseased cell is coated with bridge molecules, the more effector cells it will be able to bind. In addition, the more binding sites a bridge molecule has for the costimulatory molecules, the more effector cells it will be able to bind.

In that regard, Applicant has found that a cellular vaccine may be prepared without the need of cytokine treatment (to increase the levels of primary and costimulatory T cell activation molecules) when a plurality of bridge molecules are attached to a target cell with binding sites for two or more different costimulatory molecules on the surface of T cells (e.g., CD3, CD28, and 4-1BB). Individual bridge molecules may be attached to different anchor molecules on the surface of the target diseased cell. An individual bridge molecule may also have two or more binding sites for two or more different costimulatory molecules on the surface of T cells.

Thus, in a second aspect, this invention features an immunogenic composition containing an autologous target diseased cell having attached thereto (a) a bridge molecule which has two or more binding sites for two or more different effector cells, (b) a bridge molecule which has two or more binding sites for two or more different costimulatory molecules on the surface of effector cells, (c) two or more bridge molecules each containing a binding site for a different effector cell, (d) two or more bridge molecules each containing a binding site for a different costimulatory molecule on the surface of effector cells, (d) two or more bridge molecules each attached to a different antigen on the target cells, or (e) a combination of two or more of the above.

A pharmaceutically effective amount of an immunogenic composition of this invention may be complemented by a pharmaceutically acceptable carrier before administration to a patient mammal.

Alternatively, a patient may be administered with a pharmaceutical composition containing (1) a pharmaceutically effective amount of a cytokine capable of increasing the level of one or more primary and costimulatory T cell activation molecules in tumor cells, (2) a pharmaceutically effective amount of a bridge molecule containing a binding site for an antigen on the surface of the tumor cells and a binding site for a costimulatory molecules on the surface of T cells, and (3) a pharmaceutically acceptable carrier.

In treating a patient, the autologous target cell may be treated with cytokines or other means of increasing primary and costimulatory T cell activation molecules in vitro before the target cell is administered to the patient. Alternatively, the cytokines may be administered to the patient to increase primary and costimulatory T cell activation molecules in vivo.

In a third aspect, this invention features a method of generating cytotoxic leukocytes against diseased cells in a patient mammal by contacting a population of effector cells (e.g., white blood cells) in vitro with immunogenic compositions described above for a time period sufficient to react with the immunogenic compositions and collecting the treated effector cell population. The cytotoxic leukocytes so generated can then be administered to a patient to treat or prevent diseases. This adoptive immunotherapy can be used alone or in combination with vaccination to treat or prevent diseases.

The method of the invention is useful for the prevention and treatment of diseases which develop and/or persist by escaping immune responses triggered by T cell activation. Such diseases include, for example, all cancers, natural and induced immune deficiency states, and diseases caused by infections with a variety of pathogens. The method of the invention is illustrated herein by demonstrating its application to three different types of human cancers. Cancer cells are by nature generally weakly immunogenic, fail to trigger an effective T cell response, and survive and grow as a result. As demonstrated herein, cancers can be prevented, and established cancers may be cured, by stimulating an effective T cell response using autologous tumor cell vaccines of the invention.

Other features and advantages of the invention will be apparent from the following detailed description of the invention, and from the claims.

DETAILED DESCRIPTION OF THE INVENTION

Figure 1:
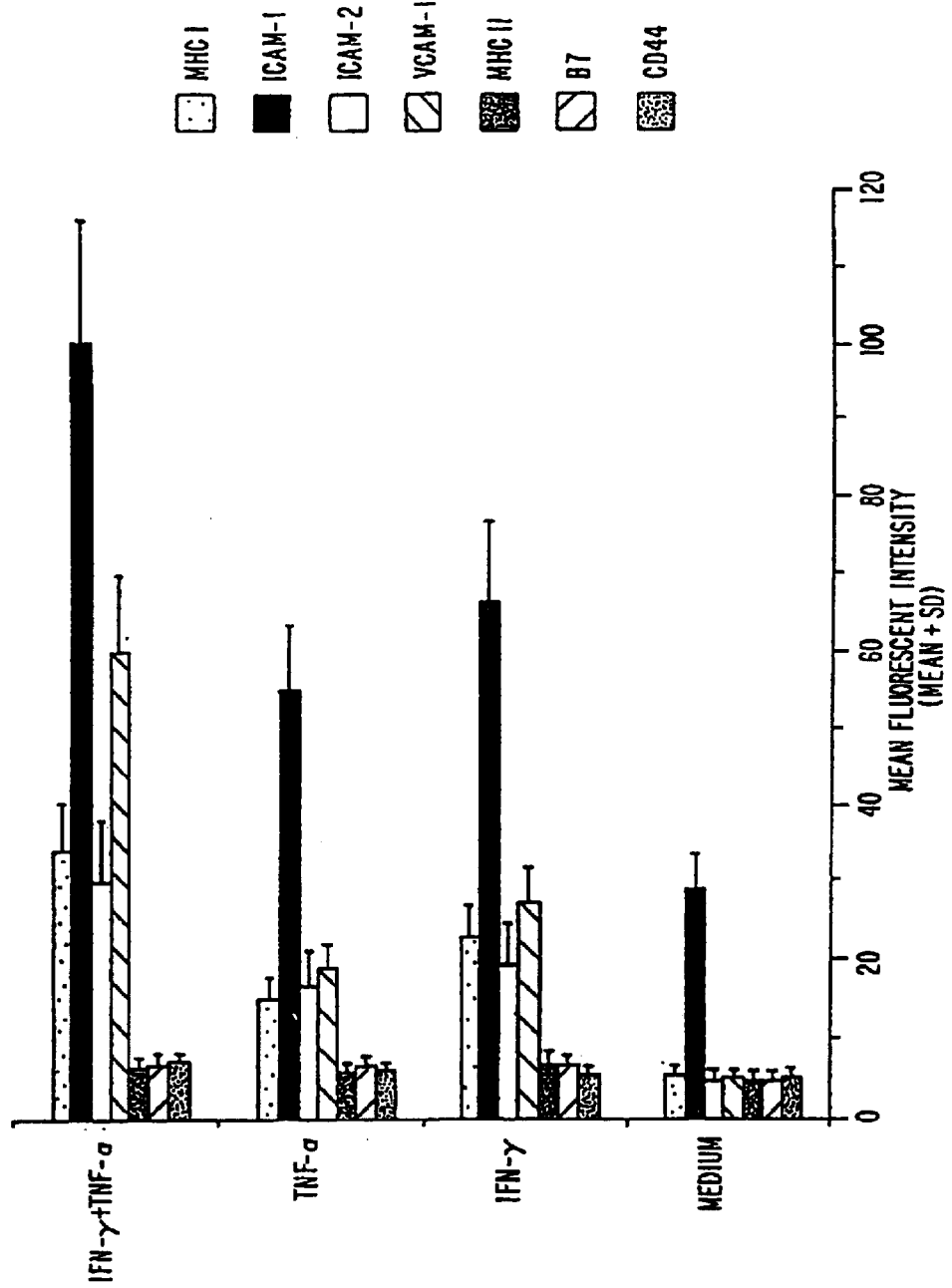
FIG. 1. Expression of MHC class I, ICAM-1, ICAM-2 and VCAM-1 antigens on cytokine treated hepa 1–6 cells. The results are representative data from four comparable experiments.

The present invention provides methods for immunizing individuals against disease and for treating individuals with established diseases using cellular vaccines created with a two-step process described herein. The methods of the invention may be applicable to any disorder involving a low- or non-immunogenic response pathology, wherein effective treatment or prophylaxis requires an immune boost through activation of T cells. Such disorders include, but are not limited to, all forms of cancer, immune deficiency disorders (both natural and induced), and infectious diseases caused by viral or other pathogenic agents.

A. Current Approaches to the Generation of Cellular Vaccines Against Tumors

Anti-tumor immune responses are primarily mediated by T cells. For optimal activation of T cells, at least two signals are essential. The first is an antigen-specific signal via the T cells receptor and MHC-polypeptide complex interaction. The second is a costimulatory signal mediated via a different set of receptor/counter-receptor pathway. Down-regulation expression of MHC and the molecules that costimulate the immune responses are associated with defective signaling of tumor cells for T cell activation. The immunogenic potential of tumor cells can be enhanced through defined molecular modifications. The modified tumor cells can be used as cellular vaccines to elicit anti-tumor specific immunity that is effective in eradicating established tumors in animals. Most of these approaches have required ex vivo or in vivo gene transfection with a viral vector or modification of tumor cells with antigen processing cells (APCs).

1). Gene Transfer to Tumor Cells

Many approaches have been used to enhance immunogenicity of tumor cells. In early studies, the stimulatory signals were provided exogenously by immunizing animals with tumor cells mixed with adjuvants or with chemically modified tumor cells. Recent advances in genetic engineering allow the modification of tumor cells by gene transfection. For example, transfection of MHC genes into tumor cells converted non-immunogenic tumor cells into immunogenic ones (Haddada et al., *Proc Natl Acad Sci USA* 1986, 83:9684–9688; and Wallich et al., *Nature* 1985, 315:301–315). Immunization of animals with tumor cells transfected with cytokine genes, including IL-1 (Z_ller et al., *Intl J Cancer* 1992, 50:450–457), IL-2 (Bubenik et al., *Immunol Lett* 1990, 23:287–292), IL-4 (Tepper et al., *Cell* 1989, 57:503–512), IL-6 (Porgador et al., *Cancer Res* 1992, 52:3679–3683), IL-7 (Hock et al., J Exp Med 1991, 174:1291–1298), TNF (Asher et al., J Immunol 1991, 146:3227–3235), G-CSF (Colombo et al., *J Exp Med* 1991, 173:889–897), GM-CSF (Dranoff et al., *Proc Natl Acad Sci USA*. 1993, 90:3539–3543), IP-10 (Luster et al., *J Exp Med* 1993, 178:1057–1065) and IFNγ (Gansbacher et al., *Cancer res* 1990, 50:7820–7825) also induced host anti-tumor immune responses. In some of these studies, anti-tumor immunity was mediated by T lymphocytes. In other studies, anti-tumor immunity was mediated by macrophages or neutrophils. Inhibition of insulin like growth factor production by transfection with a vector expressing anti-sense IGF-I rendered rodent C6 glioma more immunogenic (Trojan et al., *Science* 1993, 259:94–96).

Tumor cells (J558L) were engineered to over-produce one of 5 different cytokines (IL-2, IL-4, IL-7, TNF, or IFNγ (Hock et al., *Cancer Res* 1993, 53:714–716). These cytokine producing tumor cells were then used to immunize animals against a challenge with parental tumor cells. Injection of all cytokine producing tumor cells induced systemic responses capable of mediating the rejection of parental tumor cells when injected in low numbers.

Gene transfection approaches usually require the establishment of cells in tissue culture and transfection of primary tumor cells and selection in vitro. They are time-consuming and costly. The clinical application may thus be limited.

To circumvent requirements for the establishment of tumor cell lines in vitro, the direct introduction of genes into tumor cells in situ has been attempted. A gene encoding an allogeneic HLA antigen was incorporated into liposome, and injected into five patients with advanced melanoma. One patient demonstrated regression of tumor nodules. In this patient, metastatic lesions at distant sites also displayed complete regression. The other four patients did not respond to the treatment. These results suggest that introduction of exogenous genes directly into tumors has potential as a therapeutic approach (Nabel et al., *Ann. NY Acad Sci* 1995, 27:227–231).

2). Antigen Presentation by APCs

An effective tumor vaccine should have all the signals essential for T cell activation. Activated B cells are very effective antigen-presenting cells. In addition to expressing of high levels of MHC class II antigens, activated B cells express high levels of accessory and costimulatory molecules. In one approach, BERH-2 cells, a chemically induced rat hepatoma cell line, were fused with in vivo activated B cells. The hybrid tumor cells expressed high levels of MHC class I, II, ICAM-1 and B7 and lost tumorigenicity in syngeneic animals. Animals immunized with the hybrid cells generated by fusion of tumor cells with either activated B cells or dendritic cells became resistant to parental tumor challenge and cured established tumors (Toffaletti et al., *J Immunol* 1983, 130:2982–2986; and Guo et al., *Science* 1994, 263:518–520).

Dendritic cells transfected with tumor antigen expressing nucleic acids were able to be used as tumor cellular vaccines to stimulate T cell immunity (Liu, 1998, *Nature Biotechnology* 16:335). Several recent papers have showed that autologous dendritic cells pulsed ex vivo with tumor antigens including tumor associated antigen or tumor specific idiotype protein were able to be used as tumor cellular vaccines to stimulate host immunity (Young et al., *J. Exp. Med.* 1996, 183:7–11; Celluzzi et al., *J.Exp. Med.* 1996, 183:283–287; Hsu et al., *Nature Med.* 1996, 2(1): 52–58; and Gong et al., *Nature Med.* 1997, 3(5): 558–561). In contrast to gene transfection experiments in which only one or two genes can be introduced into tumor cells at a time, fusion of tumor cells with APCs or modification of dendritic cells with tumor antigens ex vivo gives rise to treated APCs with both tumor specific and costimulatory signals. However, these approaches are still time-consuming and requiring large numbers of activated B cell and dendritic cells.

B. Improvement and Alternative to the Current Approaches

The present invention provides improvements and alternatives to the current approaches to generate cellular vaccines against cancer and other diseases.

In one embodiment, the methods of the invention comprise modifying antigen-presenting cells (APCs) by (1) treating the APCs in order to present on the cell surface thereof antigens derived from or associated with the target diseased cells, and (2) attaching to the APCs a bridge molecule capable of binding to one or more T cell activation costimulatory molecules on the surface of T cells (e.g., CD28), thereby providing the APCs with the capacity to physically link to T cells and activate the costimulatory signal. For the first step, the APCs may be (a) transfected with foreign nucleic acid capable of expressing within the APCs antigens derived from or associated with the target diseased cells (e.g., Donnelly et al, 1994, *J. Immunol. Methods* 176:145), (b) pulsed with tumor lysate (e.g., Nestle et al., 1998, *Nat. Med.* 4:238), or (c) pulsed with purified tumor associated peptides or proteins (e.g., Mayordomo et al., 1995, *Nat. Med.* 1:1297; Porgador et al., 1995, *J. Exp. Med.* 182:255; Celluzzi et al., 1996, *J. Exp. Med.* 183:283; Paglia et al., 1996, *J. Exp. Med.* 183:317; Bakker et al., 1995, *Cancer Res.* 55:5330; Hsu et al., 1996, *Nat. Med.* 2:52; Reeves et al., 1996, *Cancer Res.* 56:5672; Zitvogel et al., 1996, *J. Exp. Med.* 183:87; and Boczkowski et al., 1996, *J. Exp. Med.* 184:465).

In another embodiment, the methods of the invention comprise modifying weakly- or non-immunogenic autologous cells of the disorder (target cells) by (1) treating the target cells in order to amplify primary and costimulatory T cell activation signals therein, and (2) attaching to the target cells a substance capable of binding to one or more antigens on the target cells and to one or more T cell activation costimulatory molecules on the surface of T cells (e.g., CD28), thereby providing the target cells with the capacity to physically link to T cells and activate the costimulatory signal. Such substances include, but are not limited to, bispecific monoclonal antibodies (Bi-MAbs) targeted to antigen on the treated cells and to CD28 and/or other costimulatory molecules on T cells.

The first step of the method amplifies the expression of cell surface molecules involved in T cell activation, such as MHC and adhesion molecules, and up-regulates antigen processing capacity within the target cells by enhancing enzyme activity involved in intracellular antigen processing. For the first step of the method, any means which can amplify primary and costimulatory T cell activation signals in the target cells (e.g., the expression of MHC and adhesion molecules), may be used. Such amplified expression may be achieved by, for example, in vitro and in vivo treatment of target cells with cytokines or other factors capable of inducing the desired amplification; and in vitro and in vivo transfer of MHC genes, adhesion molecule genes, cytokine genes, and/or MHC, adhesion molecule, and cytokine gene transcription activators or enhancers to the target cells. Specific examples include (a) introduction of gene encoding MHC Ags (Restifo et al., 1993, *J. Immunother.* 14:182; Ostrand-Rosenberg et al., 1990, *J. Immunol.* 144:4068; and Armstrong et al., 1997, *Proc. Natl. Acad. Sci. USA* 94:6886), costimulatory molecule (Chen et al., 1992, *Cell* 71:1093; Townsend et al., 1993, *Science* 259:368; Baskar et al., 1993, *Proc. Natl. Acad. Sci. USA* 90:5687; and Johnston et al., 1996, *J. Exp. Med.* 183:791), or cytokines (Fearon et al., 1990, *Cell* 60:397; Golumbek et al., 1991, *Science* 254:713; and Dranoff et al., 1993, *Proc. Natl. Acad. Sci. USA* 90:3539) into tumor cells; (b) fusion of tumor cells with antigen presenting cells (APCs) (Guo et al., 1994, *Science* 263:518; WO 95/16775; Gong et al., 1997, *Nat. Med.* 3:558; and Wang et al., 1998, *J. Immunol.* 161:5516); and (c) stimulation with virus infection (Von Hoegen, et al., 1990, *Cell. Immunol.* 126:80; Ockert et al., 1996, *Clin. Cancer Res.* 2:21; Ertel et al., 1993, *Eur. J. Immunol.* 23:2592; and Jurianz et al., 1995, *Int. J. Oncol.* 7:539).

In one embodiment of the method, amplification of primary and costimulatory T cell activation signals in the target cells is achieved using cytokine treatment. Target cells may be treated with cytokines ex vivo or in vitro as described in the examples herein. Alternatively, cytokines may be administered to the target cells in vivo by, for example, intralesional injection, intralymph injection, intravesical injection, subcutaneous injection, etc., in suitable pharmaceutical carriers or controlled release preparations. Any cytokine or combination of cytokines which results in the amplified expression of MHC and adhesion molecules may be used to treat cells in the first step of the method. In preferred embodiments, described more fully by way of the examples herein, a combination of interferon (IFN-γ) and tumor necrosis factor-α (TNFα) is used in the first step. Preferably, cells may be treated with concentrations of between about 10–100 U IFN-γ in combination with concentrations of between about 10–100 U TNFα, more preferably with 100 U IFNγ, and 50 U TNFα, as described in Example 1. However, the conditions and specific cytokines most optimal for the amplification of activation signals on the particular cells to be treated may vary and may be determined essentially as described in Example 1.

The second step of the method of the invention provides the treated cells with the capacity to physically bridge to T cell surfaces via CD28 and/or other T cell costimulatory molecules, thereby providing optimal conditions for stimulating T cell activation. For the second step, any substance capable of binding to one or more antigens on the treated cells and to one or more T cell activation costimulatory molecules on the surface of T cells may be used. Such bispecific or multispecific bridging substances may comprise, for example, Bi-MAbs, proteins and other macromolecules, and polymer materials, which contain a functionality capable of binding to the targeted T cell costimulatory molecule and activating, or inducing the activation of, the costimulatory signal. In one embodiment, described by way of the examples in Example 6, Bi-MAbs are used as the bridging substance.

One functionality of the bispecific or multispecific bridging substance may be directed to a target cell-specific antigen or any antigen expressed on the target cells. Optimally, where the target cells are to be armed with bridging substance in vivo, the target cell antigen to which the bridging substance is directed should be unique.

However, the target cell antigen need not be unique to the treated cells, since the attachment of the bridging substance may be practiced in vitro. Accordingly, bridging substances attached to the target cells in vitro will not cross-react with the same antigen on cells in the individual to be immunized with the modified cells.

After such bridging substances are incubated with cells treated according to the first step of the method, free bridging substance may be washed away and bound bridging substance may be cross-linked to the cell surface with polyethylene glycol (PEG) or another cross-linking agent.

Another functionality of the bispecific or multispecific bridging substance is specifically directed to a T cell activation costimulator such as CD28. Thus, when the modified cells are used to immunize an individual, the CD28 (or other costimulatory molecule) binding sites of the attached bridging substance are free, and will bind to CD28 (or other costimulatory molecule) on T cell surfaces, ensuring that the modified cells will become physically linked to T cells. This bridging substance-mediated physical link also brings other molecules on the surfaces of the modified cells, some of which have been amplified by the cytokine treatment step, into contact with other molecules on the surfaces of T cells, providing further costimulation which thereby further facilitates T cell activation.

The second step of the method may be practiced in vitro or in vivo, depending upon whether target cells were treated according to the first step of the method in vivo or in vitro, the circumstances of the disease or lesion to be treated, and the clinical objectives of the treatment. Where the first step of the method is conducted in vivo, the treated cells may be armed with the bridging substance in vivo as well. In this case, the clinician may use a variety of known methods for administering the bridging substance to a patient. The best route of administering the bridging substance to patients who have had disease- or lesion-specific cells (target cells) treated in vivo according to the first step of the method will depend on clinical and/or other aspects of the disease or lesion to be treated as well as on the site of the treated cells. For example, where target cells located in lymph node have been treated in vivo, direct administration of the bridging substance to the lymph node is preferred. Similarly, for example, where tumor cells have been treated in vivo by intratumor injection of cytokines or gene transfer vectors, the bridging substance preferably should be administered directly into the tumor or to the local environment of the tumor.

Where the first step of the method is conducted in vitro, the treated cells may be armed with the bridging substance in vivo or in vitro. Where the bridging substance is administered in vivo, the same route used to administer the treated cells or a similar route should be used, taking into account the same factors discussed above regarding in vivo arming of in vivo treated target cells.

When in vitro treated cells are armed in vitro, the treated and armed cells (cellular vaccine) may be used in vivo for treatment and prevention of disease, or in vitro for generation of lesion- or disease-specific cytotoxic T lymphocytes (CTLs). Arming treated cells in vitro provides the advantage of being able to use a bridging substance directed to any antigen on the target cell.

When used for treatment or immunization of a patient, in vitro treated and armed cells may be administered to the patient using a variety of methods known to those skilled in the art. In a particular embodiment, described more fully in the examples which follow, in vitro treated and armed cells are administered subcutaneously. In another embodiment, the treated and armed cells are administered by direct intralesion injection, an administration route that may provide advantages over subcutaneous administration in certain circumstances (for example, where the lesion to be treated is not well vascularized, is inaccessible for biopsy, or cannot be disrupted without creating further risk to the patient). In a further embodiment, the treated and armed cells are administered by injection into the lymph nodes. This method of administration requires fewer treated and armed cells than may typically be required using other routes of administration. Such intralymph administration may be preferred in situations where only limited autologous tissue can be obtained from a lesion using thin needle biopsy techniques (e.g., inaccessible/inoperable cancers). Moreover, intralymph administration is likely to enhance the interaction between the cellular vaccine and T cells given the large number of T cells within lymph nodes. Applicant's initial experimental data indicates that a single intralymph injection of as few as $1 \times 10^4$ cellular cancer vaccine cells, prepared using the method of the invention, can induce an effective immune response against parenteral tumor cell challenge and can cure established tumors. The therapeutic efficacy of this method of administration appears equivalent to that achieved using 100-times more cells administered subcutaneously.

In a specific embodiment of the method of the invention, Bi-MAbs that react with CD28 are used as a bispecific bridging substance. B7 interacts with both CD28 and CTLA-4 on T cells. Under certain circumstances, the B7-CTLA-4 interaction generates a negative signal which prevents T cell activation. Thus, by immunizing with cells coated with Bi-MAbs specific for CD28, the interactions between B7 on such cells and CTLA-4 (or other T cell activation down-regulating molecules) is minimized and/or bypassed. In addition, Bi-MAbs reactive with other costimulatory T cell surface molecules (e.g., CD2, CD48) may also be used in the practice of the method of the invention. Furthermore, more powerful costimulation may be achieved by using a multiplicity of Bi-MAbs having specificity for various T cell costimulators.

Bridging substances may be prepared using well known technologies. As shown in the examples which follow, Bi-MAbs may be used effectively as the bridging substance. Such Bi-MAbs may be generated using methods well known in the art, such as, for example, those described in Example 2, and as described in the references cited therein. Bi-MAbs containing multiple T cell costimulatory molecule binding sites may be prepared by chemical linkage in order to provide a means for generating multiple costimulatory activation circuits.

In addition to Bi-MAbs, molecules engineered to contain functional binding sites specific for both the antigen(s) of the target cell(s) and the T cell costimulatory molecule(s) may be used as the bridging substance in the practice of the method of the invention. Such molecules may, for example, comprise proteins, other macromolecules, and polymers engineered to contain the desired binding sites, and may be prepared by using genetic engineering technologies, synthetic technologies, or by chemical linkage of component polypeptides, polymers, and/or other macromolecules. The binding site components of such bridging substances may comprise, for example, Fab2 antibody fragments, antibody binding sites, natural or engineered ligands, or other factors reactive with the target cell antigen(s) and T cell costimulatory molecule(s).

The bridging substance may be administered to a patient in vivo using a pharmaceutically acceptable carrier or a variety of drug delivery systems well known in the art. As an example, for cancer immunotherapy, a combination of the cytokines TNFα and IFNγ and an anti-CD28 Bi-MAb may be formulated within a controlled release preparation which is administered to the patient by directly injecting the preparation into the lymph nodes or into the tumor itself.

The method of the invention is particularly useful in treating cancers. This aspect of the invention is more fully described by way of the examples presented in Example 6. The data presented in the examples indicate that strongly immunogenic tumor cells can be generated using the two-step method of the invention, comprising (1) in vitro treatment of autologous tumor cells with a combination of γ-interferon (IFNγ) and tumor necrosis factor-α (TNFα), and (2) pre-incubation with a Bi-MAb specific for both an antigen on tumor cells and CD28 on T cells. The resulting modified tumor cells are able to act as a cellular vaccine that elicits CTL-mediated immunity which can both prevent and cure established tumors. Autologous cancer cells and other diseased cells can be removed from patients by surgery or other techniques, such as fine needle biopsy, including, but not limited to, devices and methods described in U.S. Pat. Nos. 5,669,394, 5,655,541, 5,241,969, 5,060,658, 4,989,614, 4,697,600, and 4,605,011, incorporated by reference herein.

In particular, the studies described in the examples which follow show that cytokine-treated, anti-CD28 Bi-MAb-armed hepatoma cells induce protective immunity against parental tumor cell challenge and, moreover, cure established gross hepatomas in mice. In addition, the studies described in Example 7, show that the method of the invention also induces protective immunity against lymphoma and colon carcinoma.

Different routes of administration, or combinations thereof, may be preferred when treating different cancers or other diseases using the cellular vaccines of the invention. As illustrated by the study briefly described in Example 4, immunization with cytokine-treated (and un-armed) cells followed by intravenous administration of an anti-CD28 Bi-MAb induces some anti-tumor immunity in the hepatoma model system.

In comparison, as shown by the results of the studies described in Examples 5 and 6, the administration of cells treated with cytokines in vitro and armed with Bi-MAbs in vitro induces uniform tumor immunity and cures established hepatomas. It is possible that insufficient localization of the Bi-MAbs to the tumor tissue following intravenous injection in the former case is responsible for the difference in therapeutic efficacy.

Individuals may be immunized against a variety of diseases with cytokine-treated, anti-CD28 Bi-MAb-armed autologous cells, thereby providing the individual's immune system with a signal sufficient to activate T cells and confer protective immunity. Similarly, individuals may be treated for a variety of diseases by administering cytokine-treated, anti-CD28 Bi-MAb-armed autologous cells of the disease or lesion, thereby providing the individual's immune system with a signal sufficient to activate T cells and induce a cytotoxic T lymphocyte response. In both cases, Bi-MAbs with a specificity for other T cell costimulatory molecules may be used to arm the treated cells with a means to physically bridge to T cells in vivo.

In addition to MHC class I, ICAM-1, ICAM-2 and VCAM-1 molecules, treatment with cytokines may enhance tumor antigen processing by tumor cells, and may induce the expression of other cell surface molecules essential for T cell activation. A combination of cytokine treated hepa 1–6 cells and immobilized anti-CD28 MAb failed to stimulate splenic T cells in vitro or to induce anti-tumor immunity in vivo in applicant's model system. This suggests that the signal delivered by the interaction between CD28 and anti-CD28 MAb is not sufficient in itself to induce T cell activation.

In contrast, a strongly immunogenic response is obtained when cytokine treated tumor cells armed with anti-CD28 Bi-MAb in vitro interact with CD28 on T cells, indicating that a physical bridging function is an important component of the activation process.

In addition, the observation that cytokine treated, B7 transfected hepa 1–6 cells were not able to activate splenic T cells in vitro (Example 2) is consistent with the recent finding that B7 may interact with CTLA-4 to deliver a negative regulatory signal, and provides a strong rationale for using anti-CD28 Bi-MAbs to physically link the antigen presenting cell specifically to CD28 molecules for T cell activation.

The invention provides an effective alternative to gene transfer and tumor:APC engineering for the development of cellular vaccines. In particular embodiments of the invention, described in the following examples, the attachment of Bi-MAbs to tumor or other target cells takes place in vitro. Accordingly, the antigens on such cells need not be unique to those cells. Essentially, any antigen may be targeted. Bi-MAbs can be produced by linking anti-CD28 MAbs to Mabs that recognize any antigen expressed on the tumor or other target cell, including antigens which are also expressed on large populations of cells in the individual to be treated (e.g., lymphocytes). This approach may be particularly useful in situations where Mabs to tumor specific antigens are not available.

EXAMPLE 1

Cytokine Induced Expression of Adhesion and MHC Molecules on HEPA 1–6 Cells In vitro Hepa 1–6 is a chemically induced hepatoma originating in a C57BL/6 mouse (G. J. Darlington et al., 1980, J. Natl. Cancer Inst. 64: 809). Cells derived from this tumor grow rapidly and form subcutaneous nodules in syngeneic animals. Hepa 1–6 cells lack both MHC class I and B7 molecules on their cell surfaces and do not induce a host immune response even when transfected with genes encoding the B7-1 or B7-2 molecule.

The conditions and cytokines most optimal for the amplification of activation signals on hepa 1–6 cells were determined as follows. One ml of Hepa 1–6 cells was plated into 24 well tissue culture plates at a concentration of $2 \times 10^6$ cells/ml and incubated with either IFNγ, 100 U, or TNFα, 50 U, or a combination of IFNγ and TNFα at these same concentrations in complete RPMI-1640 medium supplemented with 10% fetal calf serum, 2 mM glutamine, 1× non-essential amino acid and 1 mM sodium pyruvate for 48 hr at 37° C. Hepa 1–6 cells incubated similarly but in medium alone were used as control.

Cells were washed with phosphate-buffered saline (PBS) and stained with rat monoclonal antibodies to mouse MHC class I (M1/42), MHC class II (M5/114), CD44 (KM81) (ATCC), ICAM-1 (HA58), ICAM-2 (3C4) and VCAM-1 (51-10C9) (PharMingen, San Diego, Calif.). To stain for mouse B7-1 (CD80) and B7-2 (CD86), we used CTLA4-Ig, a soluble fusion protein containing the variable domain of the human CTLA4 protein and the hinge, CH2, and CH3 domains of the human IgG1 constant region (Y. J. Guo et al., 1994, Science 263: 518; C. Caux et al., 1994, J. Exp. Med. 180: 1841; E. Murphy et al., 1994, J. Exp. Med. 180: 223; R. Seder et al., 1994, J. Exp. Med. 179: 299; B. Blazar et al., 1994, Blood 83: 3815; K. Hathcock et al., 1993, Science 262: 905; P Linsley et al., 1991, J. Exp. Med. 174: 561).

Cells were incubated with the antibodies or chimeric protein for 40 minutes on ice. A rat antibody to mouse CD3 (YCD3) and a soluble human CD44-Ig chimeric protein were used as a negative controls. Cells were washed three times. Fluorescent isothiocyanate (FITC)-conjugated goat antibody to rat Ig or FITC-labeled rabbit antibody to human Ig was added for an additional 40 minutes on ice. Samples were then washed, fixed and analyzed in a FACScan (Becton Dickinson, San Jose, Calif.). The mean fluorescent intensity in the negative control group (medium alone) was at background level except for ICAM-1.

Hepa 1–6 cells incubated with a combination of interferon (IFNγ) and tumor necrosis factor (TNFα) showed expression of MHC class I, intercellular adhesion molecule 2

(ICAM-2) and vascular adhesion molecule 1 (VCAM-1), and showed significantly enhanced expression of intercellular adhesion molecule 1 (ICAM-1) (FIG. 1). This pattern of expression was maintained for more than three days in vitro after removing cytokines from the medium. However, the cytokine treated hepa 1–6 cells (CT-hepa 1–6) were still able to form tumors in syngeneic animals. It was assumed that this may be because the cells were deficient in providing a CD28 mediated costimulatory signal due to absence in expression of B7.

EXAMPLE 2

Stimulation and Proliferation of Syngenic Splenic T-cells Induced by Cytokine Treated Hepa 1–6 Cells and Anti-CD28 Bi-MAb In vitro The following example demonstrates that cytokine activated Hepa 1–6 cells in combination with Bi-MAbs to CD28 and tumor cell antigens stimulate proliferation of splenic T cells in vitro, indicating that such Bi-MAbs can provide a CD28 costimulatory signal. Four Bi-MAbs, CD28:gp55, CD28:gp95, CD28:gp115 and CD28:gp210, each with one binding specificity for the CD28 molecule on T cells and a second binding specificity for one of three glycoproteins expressed on tumor cell surfaces, were prepared and used as follows.

For preparation of Mabs and Bi-MAbs, Wistar rats were immunized with $2\times10^7$ Hepa 1–6 cells in CFA. Following three additional boosts with the same cells in ICFA over an 8 week period, spleen cells from immunized rats were fused with YB2/0 rat myelomas as previously described (J. Alan & T. Robin, in: Immunochemistry in Practice, Chapter 2 (Blackwell, N.Y., 2d ed. 1988)). More than twenty Ig-producing hybridomas were selected by immunofluorescent staining. Three antibodies reacted with hepa 1–6 cells by flow cytometry analysis. These Mabs separately recognized a 55 Kd, 95 Kd, 115 Kd or 210 Kd glycoprotein expressed on most tumor cells as determined by immunoprecipitation. The Mabs were designated as anti-gp55, anti-gp95, anti-gp115 and anti-gp210, respectively.

Anti-mouse CD28 Mabs were generated by first immunizing Wistar rats with a mouse T cell hybridoma cell line expressing high levels of CD28 antigen on the cell surface. After cell fusion, hybridomas producing anti-CD28 MAb were selected with immunofluorscent analysis by FACScan. Anti-CD28 Mabs were further characterized and confirmed by immunoprecipitation and T cell proliferation and IL-2 production assays.

Hybridoma producing anti-mouse CD18 used to generate CD18:gp55 Bi-MAb was purchased from ATCC. All Mabs used in these experiments were purified by passage of ascites from nude mice over a protein G column.

Bi-MAbs were produced from these Mabs as previously described (J. A. MacLean et al., 1993, J. Immunol. 150: 1619; L. K. Gilliland et al., 1988, Proc. Natl. Acad. Sci. USA 85: 7719; C. Bode et al., 1989, J. Biol. Chem. 264: 944).

Normal splenic T cells were purified by nylon wool column. Purified T cells ($5\times10^6$/well) were co-cultured in complete RPMI-1640 medium at 37° C. for 96 hours with $5\times10^5$ irradiated (5000 roentgens) cytokine treated (as described in Example 1) or untreated hepa 1–6 cells in the presence or absence of CD28:gp55, CD28:gp95 or CD28:gp210 Bi-MAb. A CD 18:gp55 Bi-MAb that bridges CD18 on T cells to gp55 on tumor cells and a mixture of parental CD28 plus gp55 Mabs were used as controls. Cytokine treated or untreated hepa 1–6 cells transfected with B7 gene and expressing high level of B7 molecules on cell surfaces were also used as a control. The percentage of $CD3^+CD8^+CD25^+$ T cells (mean_SD) was determined by three color analysis in FACScan using Cy-ChromTM labeled anti-CD3, PE-labeled anti-CD8 and FITC-conjugated anti-CD25 antibodies (PharMingen, San Diego, Calif.).

Each of the Bi-MAbs was tested both in vitro and in vivo for its ability in combination with cytokine treatment of hepa 1–6 cells to activate tumor specific CTLs. Mouse splenic cells were cocultured with either cytokine treated or untreated hepa 1–6 cells in the presence of purified anti-CD28 Bi-MAb or control antibody, 50 mg/ml each, at 37° C. for 9 days.

Figure 2:
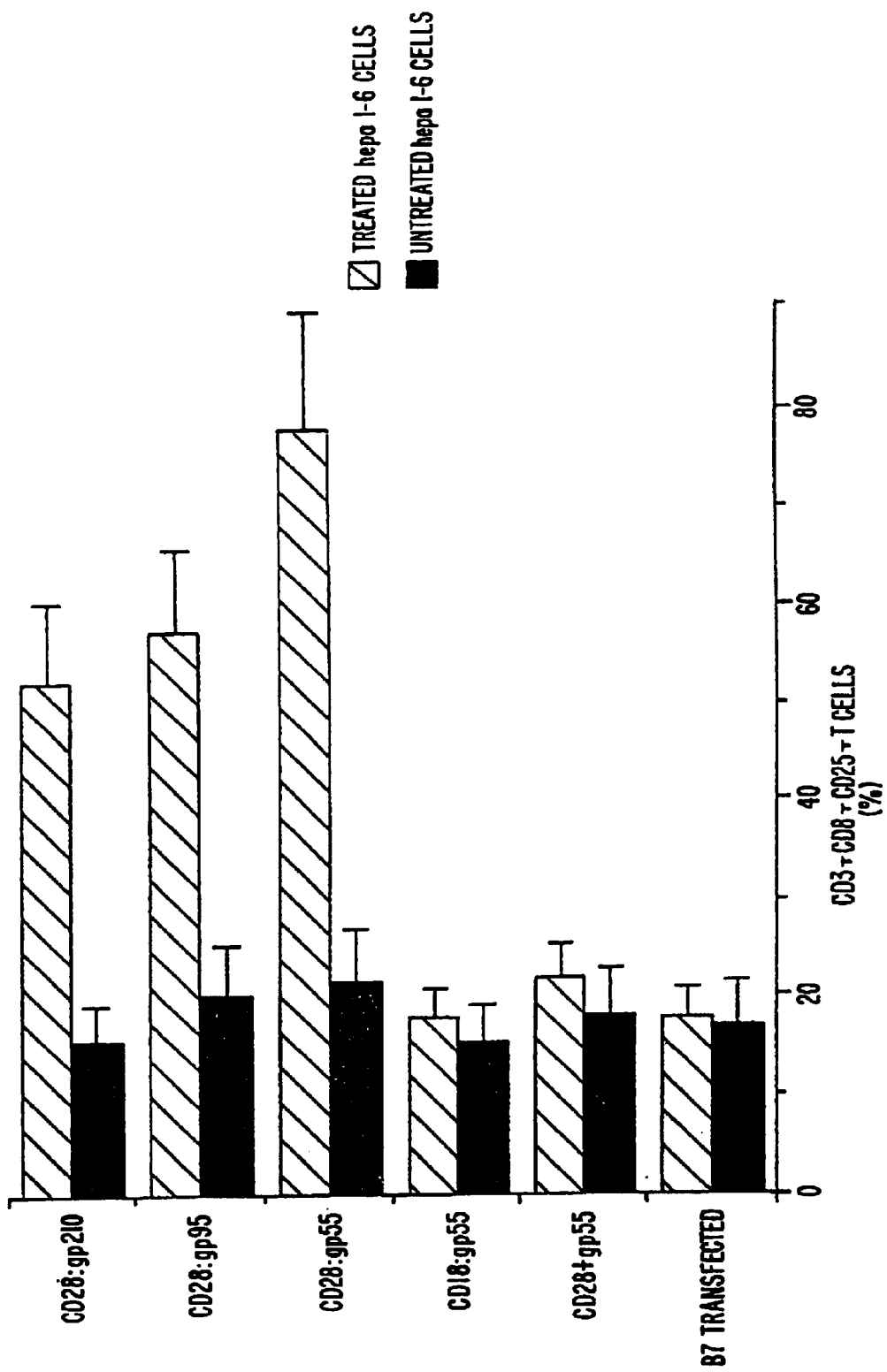
FIG. 2. Stimulation and proliferation of syngeneic splenic T cells in vitro induced by cytokine treated hepa 1–6 cells and anti-CD28 MAb.

The results presented in FIG. 2 indicate that the combination of cytokine treated tumor cells and any one of the three anti-CD28 Bi-MAbs significantly stimulated splenic T cell proliferation.

No stimulation was obtained in the absence of either anti-CD28 Bi-MAbs or the cytokine treated autologous tumor cells. Interestingly, hepa 1–6 cells transfected with, and expressing high levels of B7, were not effective in stimulating naive T cells in vitro when treated with the cytokines in similar manner. The majority of lymphocytes generated by this approach were $CD3^+CD8^+CD25^+$ T cells.

EXAMPLE 3

In vitro cytotoxicity of CTLs Generated by Cytokine Treated Hepa 1–6 Tumor Cells in Combination with Anti-CD28 Bi-MAbs Cytotoxicity of CTLs generated by in vitro priming of naive splenic T cells with cytokine treated hepa 1–6 cells in combination with anti-CD28 Bi-MAbs or control MAb was established as follows. Nylon wool-enriched naive splenic T cells ($5\times10^6$/well) were first stimulated in vitro by incubation with $5\times10^5$ irradiated (5000 roentgens) cytokine treated hepa 1–6 cells (as described in Example 1) in combination with anti-CD28 Bi-MAbs, control antibodies or irradiated B7+ hepa 1–6 alone at 37° C. for 9 days. γ-irradiated naive splenic cells ($5\times10^6$) were added into cultures as feeder cells. At the 3rd and 6th day after stimulation, 2 ml of complete RPMI-1640 medium containing recombinant human IL-2 (20 U) were added into each culture well separately.

Figure 3:
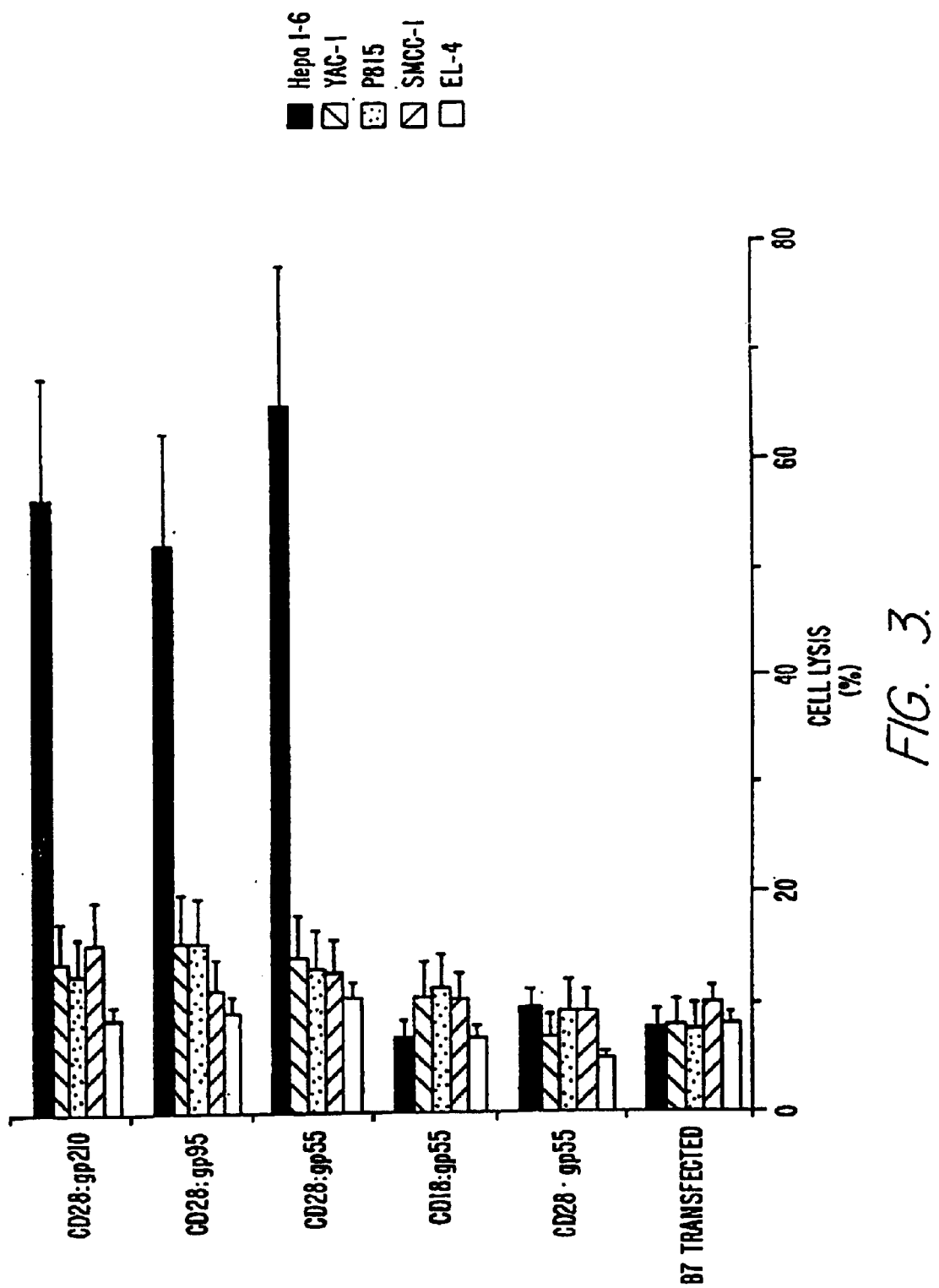
FIG. 3. Cytotoxicity of CTLs generated by in vitro priming of naive splenic T cells with cytokine treated hepa 1–6 cells in combination with anti-CD28 Bi-MAbs or control MAb.

Cytotoxicity of CTLs toward syngeneic, allogenic tumor cells and a NK sensitive YAC-1 cell line was determined in a standard 4 hour $^{51}Cr$ release assay. Results from three experiments are shown in FIG. 3 as the percentage of $^{51}Cr$ release at 1:20 E:T ratio as measure of tumor cell lysis (mean_SD). These results show that CTLs generated as described herein have cytolytic activity specific to autologous tumor cells.

EXAMPLE 4

Effect of Intravenously Administered Anti-CD28 Bi-MAbs on Tumorigenicity of Cytokine Treated Hepa 1–6 Cells Mice injected with cytokine treated hepa 1–6 cells followed by intravenous administration of anti-CD28:gp55 Bi-MAb at a dose of 100 ug on day 1, 2 and 4, experienced delayed tumor formation and 40 percent of these mice (8/20) had tumor regression. Animals injected with a combination of parental hepa 1–6 cells and anti-CD28 Bi-MAb or a combination of CT-hepa 1–6 cells and control antibody all developed tumors and died within 60 days after the inoculation of tumor cells. Immunohistological studies at 24, 48, and 72 hr after injection of the Bi-MAbs showed that the Bi-MAbs were widely distributed in lungs, liver and kidney in addition to tumor tissue.

EXAMPLE 5

Induction of Protective Immunity In vivo with Cytokine Treated Hepa 1–6 Tumor Cells Armed with Anti-CD28 Bi-MAbs Tumor cells were first treated in vitro with a combination of IFNγ, 100 U, and TNFα, 50 U, in RPMI-1640 medium with 10% fetal calf serum at 37° C., 5% $CO_2$ for 48 hours. Cells were then washed with Phosphate-Buffered Saline, PH 7.4 (PBS)×3 at 20° C. and incubated with anti-CD28 Bi-MAbs at a concentration of 50 ug/ml on ice for 45 min as described in Example 1. After an additional incubation in an equal volume of 30% polyethylene glycol (PEG) in RPMI-1640 for 60 minutes at 4° C., the cells were washed×3 as described above and suspended in a final concentration of $1-2\times10^7$/ml PBS. To arm cells with Bi-MAbs or Mabs, cytokine treated or untreated parental tumor cells were pre-incubated with respective antibodies for 45 minutes.

Five groups of C57BL/6 mice, 5 per group, were immunized subcutaneously with $1\times10^6$ cytokine treated hepa 1–6 cells armed with CD28:gp55, CD28:gp95, CD28:gp 210 or a control Bi-MAb CD 18:gp55, or with $1\times10^6$ untreated hepa 1–6 cells armed with CD28:gp55 Bi-MAb. After two weeks, mice in each of the groups were challenged with $2.5\times10^6$ parental hepa 1–6 cells injected subcutaneously.

Figure 4:
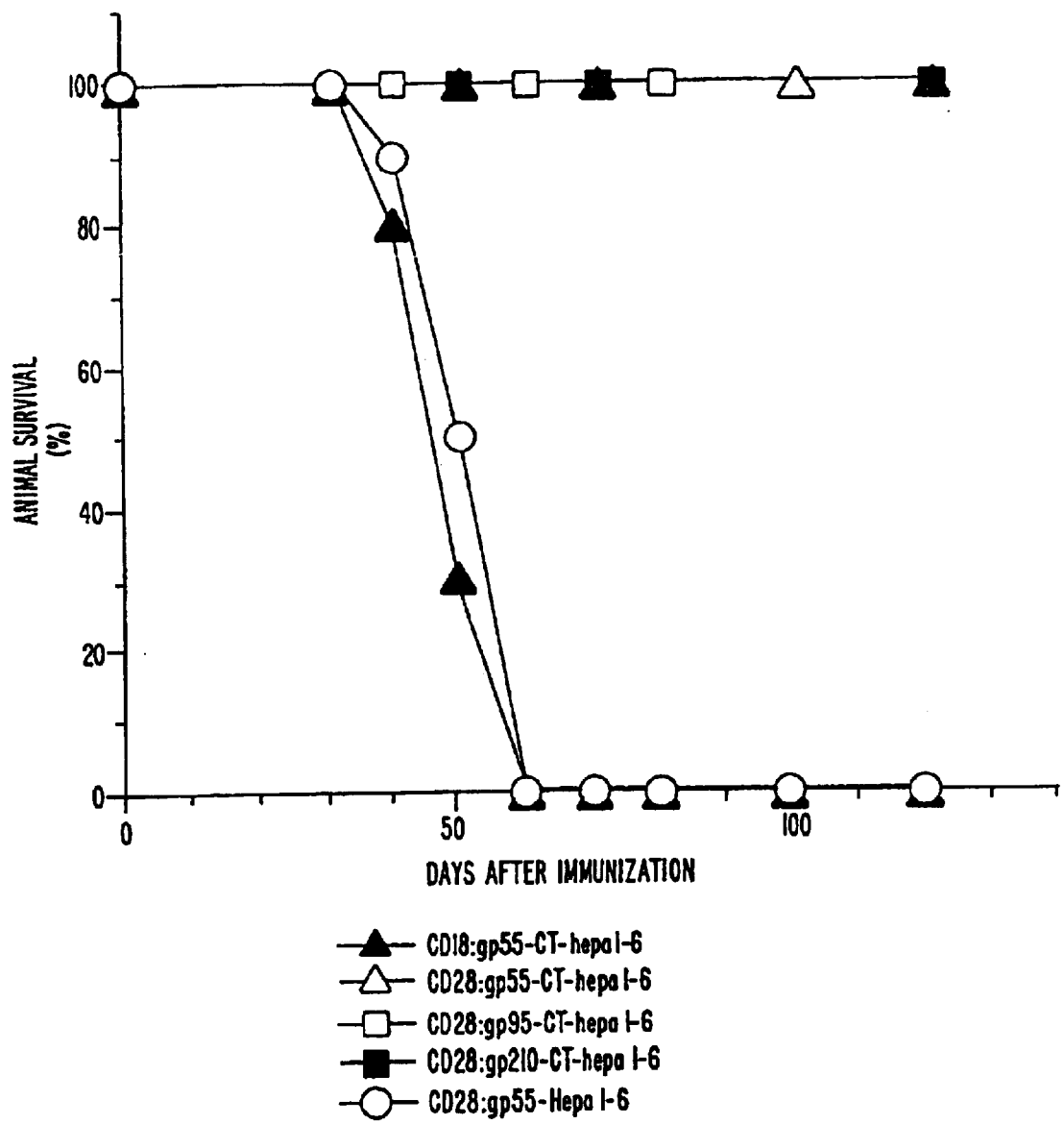
FIG. 4. Induction of protective immunity with cytokine treated hepa 1–6 cells armed with anti-CD28 Bi-MAb.

Cytokine treated hepa 1–6 tumor cells (CT-hepa 1–6) pre-incubated/armed with anti-CD28 Bi-MAbs completely lost their ability to form tumors in syngeneic mice, whereas cytokine treated hepa 1–6 cells pre-incubated/armed with control antibodies retained their tumor forming capacity. The results of the immunization experiment are shown in FIG. 4. Mice immunized with CT-hepa 1–6 cells armed with each of the CD28/tumor antigen Bi-MAbs developed protective immunity against challenge with parental tumor cells, and all of these animals remained tumor-free for 120 days after such challenge (FIG. 4). In contrast, all mice injected subcutaneously with either untreated Hepa 1–6 cells armed with anti-CD28 Bi-MAbs or CT-hepa 1–6 cells armed with the control antibody CD18:gp55 developed tumors and died within 50 days following challenge with the parental hepa 1–6 cells (FIG. 4). This experiment was repeated twice with comparable results.

EXAMPLE 6

Application of the Method of the Invention to the Hepatoma Cancer System: Cure of Established Hepaotomas with Cytokine Treated Bi-MAb-armed Hepa 1–6 Cells Vacciniation To establish that immunization with CT-hepa 1–6 cells armed with anti-CD28 Bi-MAbs can cure established hepatomas, the following three studies were performed, each of which indicates that the therapeutic administration of Bi-MAb-armed, cytokine treated hepa 1–6 cells is an effective therapy for hepatoma.

In the first study, forty mice were inoculated subcutaneously with $2\times10^6$ wild type hepa 1–6 cells. Fourteen days later, after the development of microscopic tumors, the mice were divided into four groups of ten each. The groups were treated subcutaneously with $2\times10^6$ cytokine treated or untreated hepa 1–6 cell armed with either the CD28:gp55 Bi-MAb or a control CD18:gp55 Bi-MAb.

Figure 5:
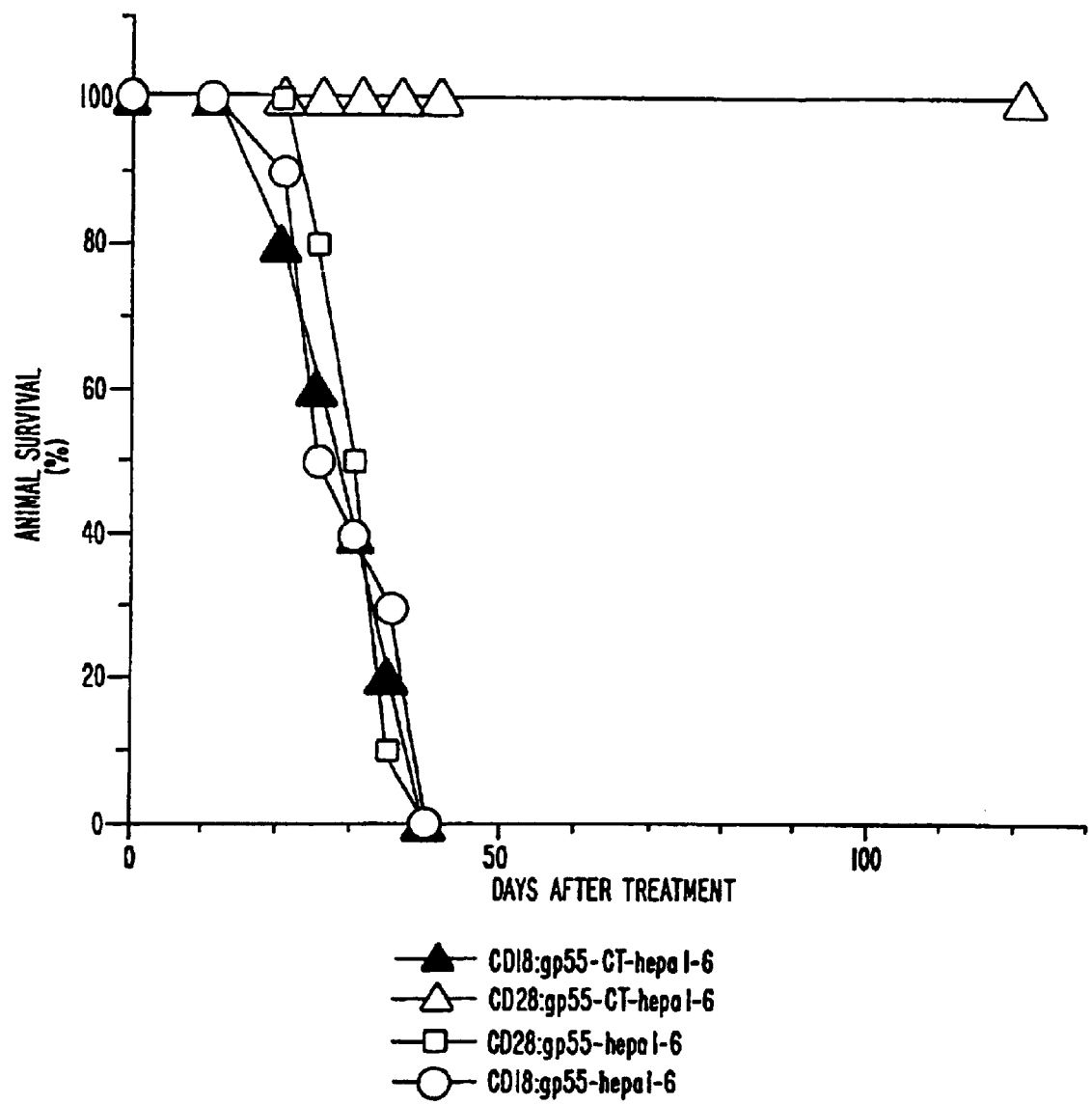
FIG. 5. Tumor rejection following treatment with cytokine treated hepa 1–6 cells armed with CD28:gp55 Bi-MAb.

The results of this study are shown in FIG. 5. All mice in the group treated with CT-Hepa 1–6 cells armed with anti-CD28 Bi-MAb survived for more than 100 days (FIG. 5). In contrast, all mice in the group treated with control Bi-MAb-armed/cytokine treated hepa 1–6 cells, and all mice in the groups treated with untreated hepa 1–6 cells armed with the CD28:gp55 Bi-MAb or the CD18:gp55 control Bi-MAb, died within about 40 days (FIG. 5). This experiment was repeated twice with comparable results.

In the second study, five groups of five mice each were injected subcutaneously with $1\times10^6$ hepa 1–6 cells. After four weeks, mice bearing tumors 6–8 mm (in the greatest dimension) were injected subcutaneously with $1\times10^6$ cytokine treated hepa 1–6 cells armed with the CD28:gp55, CD28:gp95 or CD28:gp210 Bi-MAbs, respectively[1], and then injected subcutaneously with a boost of the Bi-MAb-armed/cytokine treated hepa 1–6 cells at the same dose 7 days thereafter. Cells pre-incubated with CD18:gp55 or mixed with both anti-CD28 and anti-gp55 parental Mabs (CD28+gp55) at a concentration of 50 ug each were used as controls. Tumor size was periodically measured.

[1] hepa 1–6 can also be coated with two or more different anti-CD28 Bi-MAbs, e.g., both anti-CD28×gp55 and anti-CD28×gp95. Because hepa 1–6 cells have similar levels of expression of gp55, gp95 and gp210 antigens, the number of anti-CD28 Bi-MAbs coating the cells preincubated with two or more different anti-CD28 Bi-MAbs should be significantly higher that the pre-incubated with one anti-CD28 Bi-MAb.

Figure 6:
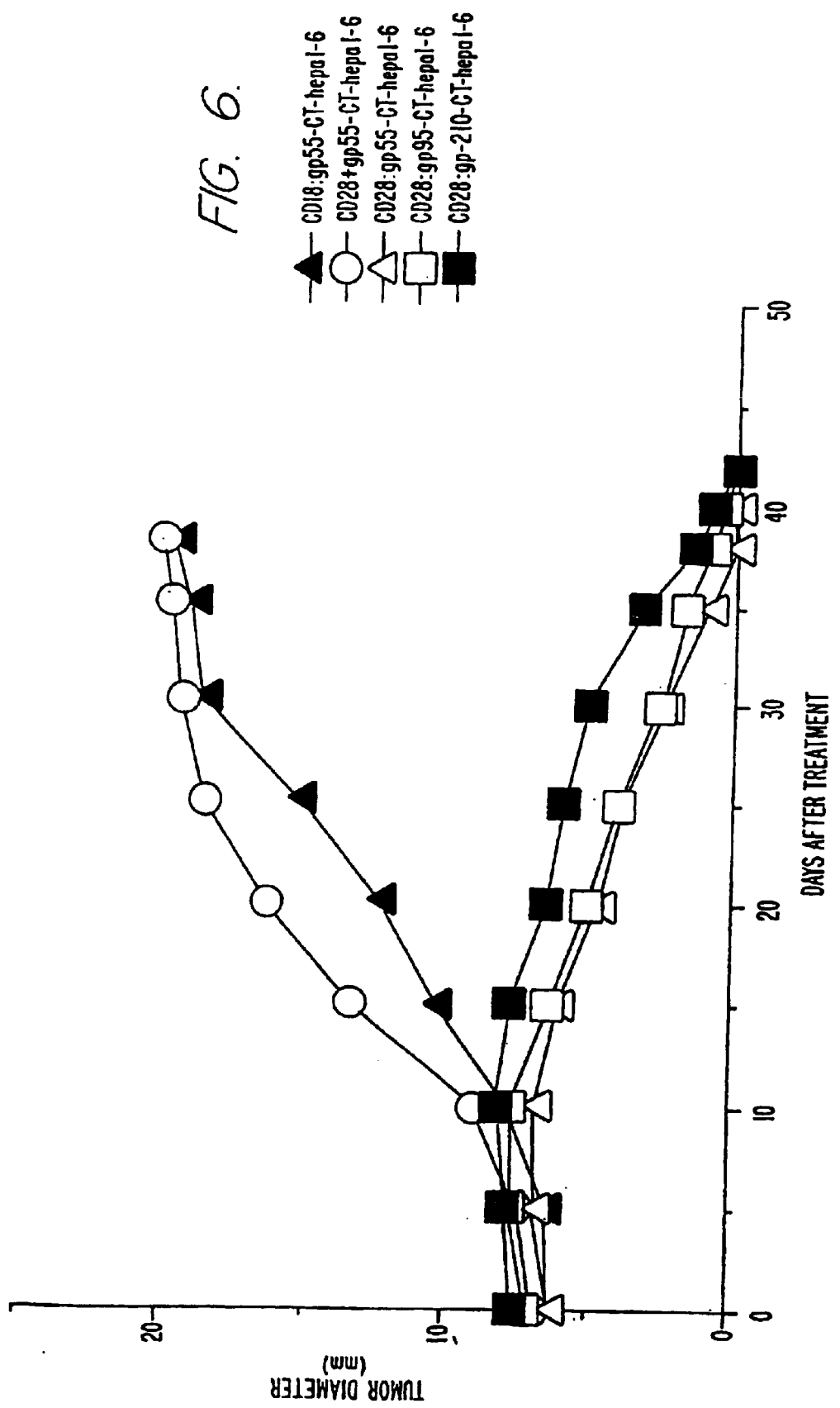
FIG. 6. Cure of established hepatomas in vivo.

The results of this study are shown in FIG. 6. Hepatomas in the mice treated with the CD28:gp55, CD28:gp95 and CD28:gp210 Bi-MAbs regressed to undetectable size within about 40 days (FIG. 6). In contrast, hepatomas in the mice treated with the CT-hepa 1–6 cells pre-incubated with either control Bi-MAb or MAb more than doubled in size within the same period, and all of these mice within that period (FIG. 6). This experiment was repeated three times with comparable results.

In the third study, γ-irradiated Bi-MAb armed tumor cells were used as the vaccine. Three groups of five mice were inoculated subcutaneously with $1\times10^6$ hepa 1–6 cells. After two weeks, mice were then injected subcutaneously either with $1\times10^6$ γ-irradiated, cytokine treated hepa 1–6 cells armed with CD28:gp55 Bi-MAb, or with a combination of y-irradiated, cytokine treated hepa 1–6 cells plus a mixture of parental anti-CD28 and anti-gp55 Mabs, or with $1\times10^6$ γ-irradiated hepa 1–6 alone.

Figure 7:
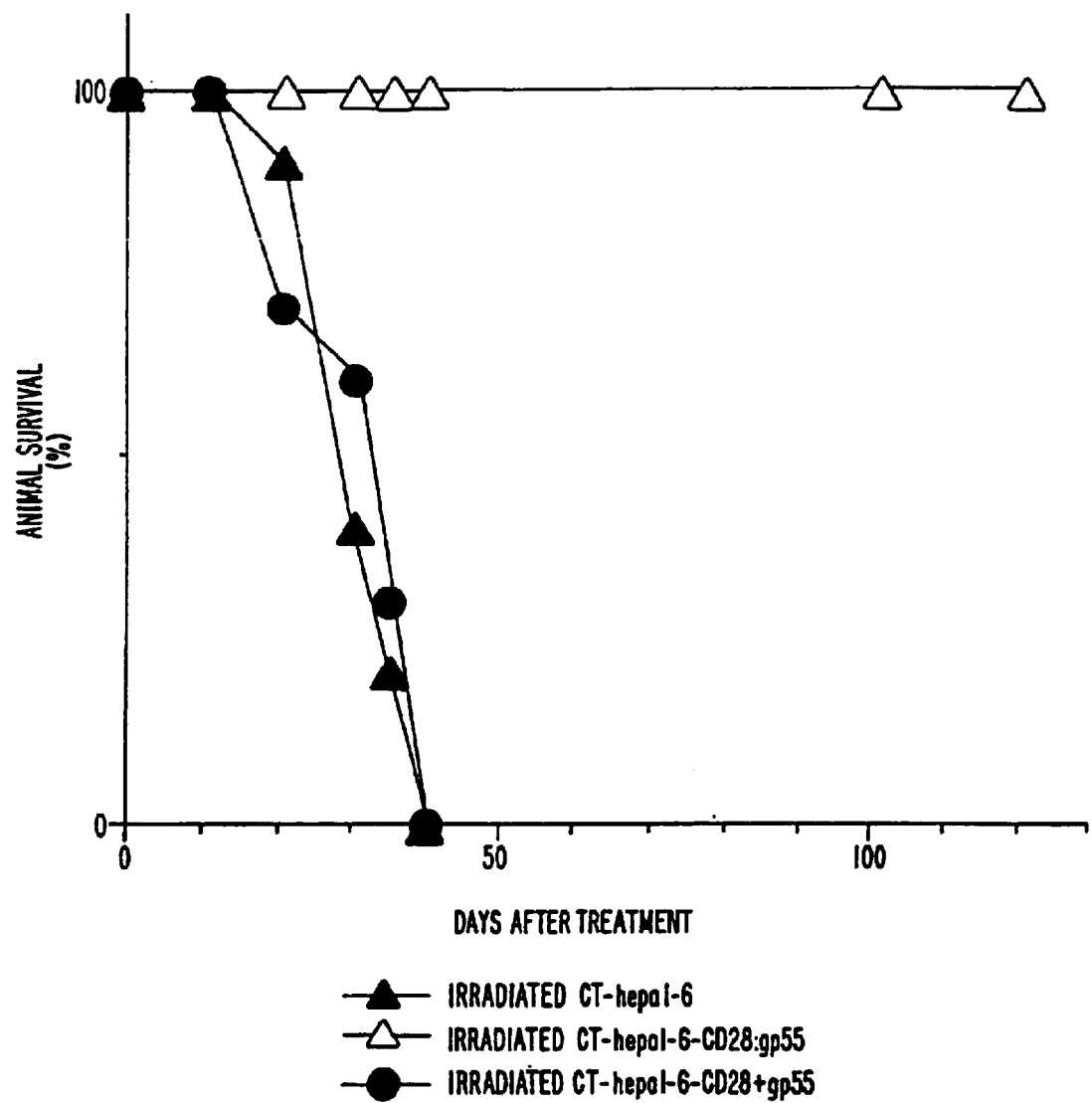
FIG. 7. Therapeutic effectiveness of γ-irradiated cytokine treated hepa 1–6 cells armed with CD28:gp55 Bi-MAb.

The results of this study, shown in FIG. 7, are similar to the results obtained in the second study described above. Only the mice treated with the γ-irradiated, cytokine treated hepa 1–6 cells armed with CD28:gp55 Bi-MAb survived (for more than 100 days). All mice in the other two groups died within 40 days of treatment.

Upon examination, tumor tissue from mice first injected with the parental tumor cells and then given cytokine treated autologous tumor cells pre-incubated with anti-CD28 Bi-MAb showed marked inflammatory responses with abundant lymphocyte infiltration. In accordance with in vitro stimulation data, the majority of the infiltrating lymphocytes were $CD3^+CD8^+CD25^+$ T cells, as determined by immunofluorescent staining of tissue sections with rat anti-mouse CD3, CD8 and CD25 MAbs. There was no local immune response in mice injected either with untreated tumor cells armed with anti-CD28 Bi-MAb or with cytokine treated tumor cells armed with control Bi-MAbs.

To further investigate if the induced immunity was mediated by CTLs, mice were depleted of CD8+T cells by antibody treatment before or after immunization. Depletion of $CD8^+$ T cells either before or after immunization abrogated the ability of the cellular vaccine to elicit anti-tumor immunity in vivo.

20–25% of infiltrating cells was $CD3^+$ $CD25^+CD4^+$ T cells. Hepa 1–6 cells were able to form tumors in 40% of mice that were depleted CD4+T cells. Therefore, induction of protective tumor specific immunity in this system requires both $CD4^+$ and $CD8^+$ T cells. After induction of protective immunity, $CD8^+$ cells can mediate tumor cell destruction alone.

Adoptive Transfer of $CD8^+$ T cells from immunized mice

To directly demonstrate that $CD8^+$ T cells from immunized mice can eradicate hepa 1–6 tumors, an adoptive transfer experiment was carried out in nude mice to reduce the numbers of $CD8^+$ T cells required for adoptive transfer. Three groups of mice were injected subcutaneously with $1 \times 10^6$ hepa 1–6 tumor cells. Two weeks after tumor cell injection, one group of mice received $1 \times 10^7$ $CD8^+$ T cells obtained from normal C57BL/6 mice. The second group received identical numbers of $CD8^+$ T cells from mice immunized with cytokine treated, anti-CD28 Bi-MAb armed hepa 1–6 cells 10 days earlier. The third group received $CD8^+$ T cells from mice immunized with cytokine treated hepa 1–6 cells pre-incubated with CD18:gp55 Bi-MAb. All mice injected with hepa 1–6 and received normal $CD8^+$ T cells or received $CD8^+$ T cells from CD18:gp55 armed, cytokine treated hepa 1–6 cells died within 50 days after tumor injection. In contrast, all mice injected with parental hepa 1–6 cells and received $CD8^+$ T cells from mice immunized with cytokine treated, anti-CD28-Bi-MAb armed hepa 1–6 cells remained tumor free for more than 100 days.

In this experiment, the spleens from normal mice, mice immunized with cytokine treated hepa 1–6 cell armed with CD18:gp55 Bi-MAbs or mice immunized with cytokine treated hepa 1–6 cells armed with CD28:gp55 Bi-MAb were removed and single cell suspensions prepared. $CD8^+$ T cells were enriched by panning of the spleen cells with plastic dishes coated with Mab specific for mouse CD8. More than 80% of the enriched lymphocytes are $CD8^+$ T cells as judged by immunofluorescent staining and analysis with FACScan.

EXAMPLE 7

Application to Additional Cancer Systems: Induction of Protective Immunity Against Lymphoma and Colon Carcinoma Using Cytokine Treated, Bi-MAb-armed Cancer Cells The immunogenicity of cytokine treated, autologous tumor cells pre-incubated with anti-CD28 Bi-MAbs was tested in two additional cancer systems, EL-4 lymphoma and SMCC-1 colon carcinoma.

The EL-4 lymphoma becomes immunogenic when transfected with the B7 gene. In contrast, SMCC-1 colon carcinoma remains non-immunogenic even after transfection with the B7 gene. Both of these cell lines grow rapidly and develop subcutaneous tumors in syngenic C57 BL/6 mice (see, for example, Li et al., 1996, J. Exp. Med. 180: 211). Both of these cell lines express the gp55 antigen on their cell surfaces. Accordingly, the anti-CD28:gp55 Bi-MAb described in the previous examples was also used in these studies.

Three groups of mice were immunized subcutaneously with $1 \times 10^6$ cytokine treated, CD28:gp55 Bi-MAb-armed, hepa 1–6, EL-4 or SMCC-1 tumor cells respectively.

After two weeks, mice immunized with the modified hepa 1–6 cells were divided into three groups and challenged by a subcutaneous injection with $1 \times 10^6$ hepa 1–6 cells, SMCC-1 cells or EL-4 cells respectively.

The mice immunized with the cytokine treated, CD28:gp55 Bi-MAb-armed SMCC-1 cells were divided into two groups. One group was challenged by subcutaneous inoculation with $1 \times 10^6$ SMCC-1 cells. The other group was challenged by subcutaneous inoculations of EL-4 cells and $1 \times 10^6$ hepa 1–6 cells into the left and right flanks of mice, respectively.

Similarly, the mice immunized with the cytokine treated, CD28:gp55 Bi-MAb-armed EL-4 cells were divided into two groups which were challenged with either EL-4 cells alone or with both SMCC-1 and hepa 1–6 cells.

The results of this study, presented in Table I below, were repeated twice with identical results.

TABLE I

Specificity of the immune responses elicited by cytokine treated and anti-CD28 Bi-MAb armed tumor cells.

| IMMUNIZATION CELLS | CHALLENGE CELLS | NUMBER OF MICE WITH TUMORS |
|---|---|---|
| Bi-MAb-CT Hepa 1–6 | Hepa 1–6 | 0 of 10 |
| Bi-MAb-CT Hepa 1–6 | SMCC-1 | 6 of 6 |
| Bi-MAb-CT Hepa 1–6 | EL-4 | 5 of 5 |
| Bi-MAb-CT SMCC-1 | SMCC-1 | 0 of 6 |
| Bi-MAb-CT SMCC-1 | EL-4 + Hepa 1–6 | 6 of 6 |
| Bi-MAb-CT EL-4 | EL-4 | 0 of 6 |
| Bi-MAb-CT EL-4 | SMCC-1 + Hepa 1–6 | 6 of 6 |

Immunization with cytokine treated EL-4 (CT-EL-4) or cytokine treated SMCC-1 (CT-SMCC-1) tumor cells armed with the anti-CD28:gp55 Bi-MAb elicited anti-tumor immunity against autologous parental tumor in all animals (Table 1).

The elicited immunity in all three experimental groups was tumor-specific. For example, immunization with CT-hepa 1–6 cells armed with anti-CD28 Bi-MAb did not inhibit growth of syngeneic EL-4 or SMCC-1 tumors in vivo (Table 1). Interestingly, in the absence of treatment with cytokines, the parental EL-4 cells expressed high levels of MHC class I at cell surfaces, yet when pre-incubated with anti-CD28:gp55 Bi-MAb, they were still not able to induce protective immunity. In addition, CTLs from mice immunized with cytokine treated autologous tumor cells armed with anti-CD28 Bi-MAbs specifically lysed the parental tumor cells but not other tumor cells in vitro.

EXAMPLE 8

Induction of Cellular Immunity by Tumors Armed with Multivalent Bridge Molecules The above data showed that SMCC-1, EL-4 and Hepa 1–6 cells became more immunogenic after treatment in vitro with a combination of cytokines and anti-CD28 bispecific monoclonal antibody. The modified tumor cells were able to elicit anti-tumor specific immunity that were both preventive and curative.

The following data showed that EL-4 and SMCC-1 cells were also effective for eliciting preventive and curative antitumor immunity in syngenic animals without cytokine treatment when these cells were precoated with two different bispecific monoclonal antibodies (Bi-MAbs), one specific for CD28 and another specific for 4-1BB.

4–1BB is a glycoprotein expressed on primed $CD4^+$ and $CD8^+$ T cells. 4-1BB signaling either by binding to 4-1BB ligand or by antibody ligation delivers a dual mitogenic signal for T-cell activation and growth (Alderson et al., 1994, *Eur. J. Immunol.* 24:2219; Hurtado et al., 1995, *J. Immunol.* 155:3360; and DeBenedette et al., 1995, *J. Exp. Med.* 181:985). It was shown that administration of anti-4-1BB monoclonal antibodies could eradicate established large tumors in mice (Melero et al., 1997, *Nat. Med.* 3:682).

The cells were coated in vitro with anti-gp55:anti-CD28 and anti-gp 115:anti-4-1BB Bi-MAbs in a concentration of 50 ug/ml on ice for 45 min. After fixed with PEG and washed for three times, the tumor cells coated with the two different Bi-MAbs were subcutaneously injected into syngenic animals at different doses. Two weeks later, the immunized animals were challenged with parental tumor cells and tumor formation rate was observed (Table II).

TABLE II

Comparison of the efficacy of immunogenic tumor cells modified with different process in vitro on eliciting preventive antitumor immunity in vivo

| Immunization | Dose | Challenge | Tumor Formation |
|---|---|---|---|
| Irradiated EL-4 Wt | $1 \times 10^6$ | $1 \times 10^6$ EL-4 Wt | 100% |
| Irradiated CT-EL-4 Wt | $1 \times 10^6$ | $1 \times 10^6$ EL-4 Wt | 100% |
| Irradiated EL-4 coated w/CD28 BiMab | $1 \times 10^6$ | $1 \times 10^6$ EL-4 Wt | 50% |
| Irradiated CT-EL-4 coated w/CD28 BiMab | $1 \times 10^6$ | $1 \times 10^6$ EL-4 Wt | 0% |
| | $1 \times 10^5$ | $1 \times 10^6$ EL-4 Wt | 20% |
| | $5 \times 10^4$ | $1 \times 10^6$ EL-4 Wt | 60% |
| Irradiated EL-4 Wt coated w/anti-CD28 & anti-4-1BB BiMabs | $1 \times 10^6$ | $1 \times 10^6$ EL-4 Wt | 0% |
| | $1 \times 10^5$ | $1 \times 10^6$ EL-4 Wt | 0% |
| | $5 \times 10^4$ | $1 \times 10^6$ EL-4 Wt | 10% |

In curative experiments, syngenic animals were first inoculated subcutaneously with $2 \times 10^6$ parental tumor cells. After two to four weeks, the tumor bearing animals were injected with the modified tumor cells. The mean survival time was monitored (Table III).

TABLE III

Comparison of the efficacy of immunogenic tumor vaccines armed with monovalent or multivalent bi-specific Mabs on eliciting curative antitumor immunity in vivo

| Tumors | Vaccination | Dose | Animal Survival (%)* |
|---|---|---|---|
| SMCC-1 | SMCC-1 Wt | $1 \times 10^6$ | 0% |
| SMCC-1 | CT-SMCC-1 + CD28 BiMabs | $1 \times 10^6$ | 100% |
| | | $5 \times 10^5$ | 30% |
| SMCC-1 | SMCC-1 + CD28 & 4-1BB BiMabs | $1 \times 10^6$ | 100% |
| | | $5 \times 10^5$ | 80% |
| SMCC-1 | SMCC-1 + CD28 & 4-1BB BiMabs (multivalent BiMabs) | $1 \times 10^6$ | 100% |
| | | $5 \times 10^5$ | 100% |
| | | $1 \times 10^5$ | 60% |

*60 day survival rate after tumor vaccine treatment.

EXAMPLE 9

Generation of Cellular Immunity Against Virus Infected Cells

Primary liver cells were obtained from clinical biopsy laboratory and cultured in hepatocellular media. Autologous peripheral blood lymphocytes were obtained from same patients during operation and cultured in complete RPMI-1640 medium supplemented with 5% human AB serum and 5% fetal calf serum, 20 iu/ml rh-IL-2.

Liver cells were infected by E1B deleted Adenovirus as reported previously. Virus infection was confirmed by RT-PCR and histological examination.

Infected liver cells were then treated in vitro with (1) cytokines alone, (2) BiMabs alone, or (3) cytokine+ bispecific Mabs. The modified virus-infected liver cells were irradiated at a dose of 5000R and were then co-cultured with autologous PBL in complete RPMI-1640 medium as reported previously.

The cytotoxicity of the CTLs generated by the unmodified and the modified liver cells was determined with a standard 4 h $^{51}$Cr release assay.

TABLE IV

Generation of cytotoxic T cells in vitro by stimulating autologous peripheral blood lymphocytes with virus-infected human fetal liver cells pretreated with a combination of INFγ and TNFα and coated with anti-CD28 bispecific monoclonal antibody

| Target cells | Treatment | Effectors | E:T Ratio | Cytotoxicity |
|---|---|---|---|---|
| Liver cells | None | PBL | 1:50 | ~3% |
| Liver cells | Cytokines | PBL | 1:50 | ~3% |
| Liver cells | BiMabs | PBL | 1:50 | ~3% |
| Liver cells | Cyto + BiMab | PBL | 1:50 | ~3% |
| Ad-Liver cells | None | PBL | 1:50 | ~3% |
| Ad-Liver cells | Cytokines | PBL | 1:50 | ~5% |
| Ad-Liver cells | BiMabs | PBL | 1:50 | ~13% |
| Ad-Liver cells | Cyto + biMabs | PBL | 1:50 | ~20% |
| Ad-Liver cells | biMabs (Multivalent*) | PBL | 1:50 | ~40% |
| Ad-Liver cells | Cyto + biMabs (Multivalent*) | PBL | 1:50 | ~40% |

*Anti-Gp115: Anti-CD28 bispecific monoclonal antibody was generated by chemical linking several anti-CD28 and anti-Gp115 monoclonal antibodies together and purified by sequential affinity columns, one specific binding gp-115 and another for CD28 monoclonal antibody specifically.

EXAMPLE 10

Generation of Humanized Bi-MAbs

The Bi-MAbs of this invention can be generated by a variety of techniques known to those skilled in the art (see, Vaughan et al., *Nature Biotechnology* 16:1015–1016; Hoogenboom, 1998, *Immunotechnology* 4:1–20; and Holliger & Hoogenboom, 1998, *Nature Biotechnology* 16:1015). (1) Recombinant chimeric antibodies comprise rodent variable (V) regions attached to human constant (C) regions. (2) In humanized (or reshaped) antibodies, only the antigen-binding complementarity-determining region (CDR) loops derive from rodent antibodies. (3) All-human antibodies can be constructed from human V regions (isolated by phage display technology) and human C regions. Fv and scFv fragments, and diabodies comprise only V regions and can be cloned from hybridomas or isolated from phage libraries. (4) All-human antibodies can also be prepared from transgenic non-human animals capable of producing human antibodies. Therefore, the techniques described in the following references can be readily used to prepare Bi-MAbs for purposes of this invention: Merchant, 1998, *Nature Biotechnology* 16:677; Holliger, 1997, *Nature Biotechnology* 15:632; McGuinness et al., 1996, *Nature Biotechnology* 14:1149; Reiter et al., *Nature Biotechnology* 14:1239; Vaughan et al., 1996, *Nature Biotechnology* 14:309; WO 98/24884; U.S. Pat. Nos. 5,814,318, 5,789,215, 5,770,429, 5,693,762, 5,530,101, 5,637,481, 5,601,819, and 5,141,736.

For example, anti-CD28 and anti-4-1BB monoclonal antibodies that costimulate human T cells can be humanized for T cell activation and the induction of antitumor immunity both in vitro and in vivo. Variable (V) domains of mouse Mab can be spliced to join the constant (C) domains of human IgG by PCR technology. The transfected cell lines producing high level of humanized Mab will be selected and the Mab will be purified to milligram quantities for testing efficacy in T cell activation in vitro and antitumor effect in vivo. Specifically, two different bispecific monoclonal antibodies will be generated and tested, antitumor antigen X CD28 and Antitumor antigen X 4-1BB.

To generate antitumor antigen X CD28 Mab, the cDNA fragment of V region of mouse Ig light (L) and heavy (H) chain is amplified by PCR from the candidate hybridomas producing anti-CD28 or antitumor antigen Mabs and inserted into plasmids that contain human Cκ and Cγ 1 region driven by CMV and β-globin major promoters, respectively. The vectors also contain neomycin and DHFR resistant gene. The resulting vector will be transfected into DHFR-negative DG44 cells and initially selected by G418 at 400 ug/ml. The clones that produce the highest amount of Ig will be further expanded and incubated with methotrexate for gene amplification. The clones resistant to methotrexate will be selected and ELISA will quantitate the Ig production in supernatant. The humanized Mabs will be purified by protein G affinity chromatography. The purified humanized antitumor antigen and antiCD28 Mabs will be used to generate bispecific monoclonal antibodies by either chemical linkage or reconstruction technology under a low salt and low PH condition as described previously.

Alternatively, single chain bispecific monoclonal antibodies (tumor antigen X CD28 and tumor antigen X 4-1BB) can be produced. Two single chain Fv fragments will be joined through a flexible Gly-Ser linker. The single chain Fv fragment directed against tumor antigen (gp115) is derived from gp115 hybirdoma; the other directed against CD28 or 4-1BB is derived from GW28 (CD28) and GW4-1BB (anti4-1BB) hybridomas. The constructs will be expressed in CHO cells as full functional molecules and will be purified via its C-terminal histidine tail on a Ni-NTA (Nitrilotriacetic acid) affinity column.

If the cytokine treated human cancer cells (e.g., melanoma and hepatoma cells) armed with humanized antiCD28 or anti-41Bb Bi-MAb can effectively stimulate T cells in vitro with generation of CTLs, they can be further tested for anti-tumor immunity in vivo. Because of different tumorigenicity of human cancer cells in vivo, three xenografted human melanoma and two hepatoma cancer models with similar tumor formation rates in have been established in scid mice and nude mice in our lab and can be used for prevention and cure experiments.

For active immunotherapy, scid and nude mice are injected with $5 \times 10^7$ autologous peripheral T lymphocytes for reconstitution of a human immune system, which will be confirmed by flow cytometery, T cell proliferation and CTLs assay. The mice will be immunized with $1 \times 10^6$ cytokine treated cancer cells armed with humanized antiCD28 or anti4-1BB Bi-MAb for three times with a 10 day period and then challenged with $1 \times 10^6$ prenatal tumor cells. For cure experiments, the mice with reconstituted human immune system will be first inoculated with $2 \times 10^6$ parental tumor cells. Two weeks after tumor inoculation, $1 \times 10^6$ cytokine treated tumor cells armed with Bi-MAb or tumor cells armed with control Bi-MAbs will be injected intravenously into each group of mice bearing tumors. Tumor growth and survival will be monitored.

For adoptive immunotherapy, human $CD8^+$ clones specific for autologous tumor cells will be generated by stimulating PBL or TILs with cytokine treated cancer cells armed with Bi-MAb in vitro. $1 \times 10^7$ CTLs will be adoptively transferred into naive or tumor bearing scid mice to evaluate the effectiveness of the T cell clones in prevention and cure of xenografted autologous human melanoma or hepatoma tumors.

If anti-tumor specific immunity can be adoptively transferred by in vitro generated CTLs, this will provide an additional opportunity to form a combined active and adoptive anti-cancer immunotherapy for human cancers. Because it has been known that immunosuppression exists in cancer patients especially in the patients with advanced cancers, it is difficult to activate T cells in vivo with active vaccine immunotherapy alone for induction of effective immunity. The combination of active and adoptive therapy can be more effective for elicitation of anti-tumor immunity.

EXAMPLE 11

Arming Fusion Tumor Vaccine with Bi-MAb to Enhance Immunogenicity

Cellular tumor vaccines can be generated by fusion of tumor cells with antigen processing cells such as activated B cells or dendritic cells. The immunogenicity of fusion tumor vaccine cells can be further enhanced by arming them with antitumor:anti-CD28 bispecific monoclonal antibody (e.g., GP55×28, GP95×28, GP115×28 or GP210×28). Without being bound by any theory, applicant proposes that the arming reduces the inhibition of T cell activation by negative signaling from the binding of B7 on fusion cells to CTLA-4 on T cells.

Briefly, fusion tumor vaccines were first produced by fusing rat NBT II tumor cells and mouse SMCC-1 cells with in vitro activated syngeneic B cells or in vitro activated syngeneic bone-marrow derived dendritic cells using a standard fusion protocol described previously (See, e.g., Guo et al., 1994, Science 263:518–520; W095/16775). Bispecific monoclonal antibody used in the experiment is GP115×CD28 that was generated by a chemical approach. After fusion, hybrid tumor cells were selected and armed in vitro with bispecific monoclonal antibody. Antitumor antigenxCD18 monoclonal antibody was used as antibody control and fusion tumor vaccine and two-step tumor vaccines were used as cellular vaccine controls. A sub-optimal E:T cell ration was used in the following experiments.

Resulting hybrid tumor cells armed with bispecific monoclonal antibody were co-cultured with syngeneic naïve T cells at different vaccine cell:T cell ratios. The proliferation of T cells was measured by a standard [$^3$H]-Thymidine incorporation assay. All cultures were done in triplicate and the numbers present in the following tables are the average of the radioactive thymidine incorporation in each triplicate.

As showed in Table V, fusion tumor vaccine cells armed with GP115×CD28 Bi-MAb in vitro had enhanced ability to stimulate naive splenic T cells at a 1:50 vaccine:T cell ratio. In contrast, both fusion tumor vaccine and two-step tumor vaccine achieved similar effect in inducing T cell proliferation at 1:25 ratio.

TABLE V

Ability of fusion vaccine in stimulating T cell proliferation is significantly enhanced by arming with GP11xCD28 Bi-MAb

| Vaccines | [$^3$H]-Thymidine incorporation/Cell ratio | | | CD3CD8CD25 |
|---|---|---|---|---|
|  | 1:100 | 1:50 | 1:25 |  |
| Rat NBT-II B | 1,700 + 400 | 2,400 + 380 | 3,800 + 1,200 | 45% |
| Rat NBT-II D | 1,980 + 700 | 2,250 + 670 | 4,100 + 1,400 | 41% |
| Rat NBT-II-B-BiMab | 2,400 + 540 | 4,900 + 1400 | 6,840 + 1,090 | 84% |
| Rat NBT-II-D-BiMab | 2,100 + 680 | 3,800 + 980 | 5,700 + 1,120 | 79% |
| Mouse SMCC-1 B | 2,240 + 840 | 2,800 + 510 | 2,890 + 780 | 38% |
| Mouse SMCC-1 D | 1,800 + 470 | 2,400 + 650 | 2.900 + 920 | 40% |
| Mouse SMCC-1 B-BiMab | 2,700 + 680 | 3,300 + 790 | 4,900 + 700 | 75% |
| Mouse SMCC-1 D-BiMab | 2,300 + 510 | 3,100 + 270 | 4,400 + 630 | 64% |

Table V. Normal naïve spleen cells were obtained from syngeneic animals and purified by Nylon wool column. Purified T cells (5 × 10$^6$/well) were co-cultured with 5 × 10$^4$, 1 × 10$^5$ or 2 × 10$^5$ irradiated (5000 roentgens) fused tumor vaccine cells or fused tumor vaccine cells armed with GP115XCD28 BiMab in complete RPMI-1640 medium supplemented with 10% fetal bovine serum, 1% L-glutamine and 20 um/ml recombinant IL-2 for 9 days. The majority of T cells generated by this in vitro approach is CD3$^+$CD8$^+$CD25$^+$ T cells indicated by immunofluorescent staining and flow cytometery analysis.

Briefly, to stimulate tumor specific CTL responses, purified spleen T cells from naive C57BL/mice were primed with γ-irradiated cytokine treated or untreated hepa 1–6 cells in the presence of Bi-MAbs or control antibodies for 9 days in complete RPMI-1640 medium supplemented with 10% fetal bovine serum, 1% L-glutamine and 20 u/ml recombinant IL-2.

Five×10$^6$ γ-irradiated syngeneic naive spleen cells were added into cultures as feeders. The cytotoxic activity of in vitro-stimulated splenocytes was determined using the $^{51}$Cr-release assay. Briefly, tumor or control target cells were labeled with 100 μCi of $^{51}$Cr for 60 min and washed three times with HBSS. Labeled target cells were incubated with in vitro-primed CTLs at various effector:target ratios in 200 μl of RPMI-1640 medium containing 10% fetal bovine serum, 2 mM glutamine, 0.5% gentamicin sulfate and 2×10$^{-5}$ M 2-mercaptoethanel. After incubating for 4 h at 37° C. in 5% CO$_2$, 200 μl of culture supernatant was collected and the amount of $^{51}$Cr released from labeled targets was determined. The percentage of cytotoxic activity at each effector:target ratio was calculated as described elsewhere.

CTLs generated by these approaches demonstrated specific cytolytic activity to autologous tumor cells as assessed by the $^{51}$Cr releasing assay (Table VI). The results show that CTLs generated by this in vitro Bi-MAb modification are tumor specific and have no cross-reaction with syngeneic tumor cells and YAC-1, a NK sensitive cell line.

TABLE VI

Specific cytotoxicity of CTLs generated by stimulating splenic naïve T cells with fused NBT cells and fused NBT cells armed with GP115xCD28 BiMab in vitro.

| Effector cells | E:T ratio (1:20) | | | |
|---|---|---|---|---|
|  | NBT-II | BERH-2 | C6 | YAC-1 |
| CTLs (Fused NBT-B) | 35% | 8% | 10% | 7% |
| CTLs (Fused NBT-D) | 33% | 10% | 11% | 8% |
| CTLs (Fused NBT-BxBiMab) | 67% | 12% | 12% | 10% |
| CTLs (Fused NBT-DxBiMab) | 55% | 10% | 13% | 11% |

TABLE VI-continued

Specific cytotoxicity of CTLs generated by stimulating splenic naïve T cells with fused NBT cells and fused NBT cells armed with GP115xCD28 BiMab in vitro.

|  | SMCC-1 | Hepa 1-6 | P815 | YAC-1 |
|---|---|---|---|---|
| CTLs (Fused SMCC-1-B) | 28% | 5% | 6% | 4% |
| CTLs (Fused SMCC-1-D) | 21% | 6% | 5% | 5% |
| CTLs (Fused SMCC-1BxBiMab) | 50% | 8% | 7% | 7% |
| CTLs (Fused SMCC-1DxBiMab) | 44% | 5% | 8% | 4% |

Table VI. Nylon wool-enriched naïve splenic T cells (5 × 10$^6$/well) were first stimulated by incubation with 2 × 10$^5$ irradiated (5000 roentgens) fused tumor vaccine cells or fused tumor vaccine cells armed with GP115xCD28 BiMab in vitro. Cytotoxicity of CTLs toward syngeneic, allogenic tumor cells and a NK sensitive YAC-1 cell line was determined in a standard 4 hour $^{51}$Cr releasing assay. Results from three experiments are shown as the percentage of $^{51}$Cr release as measure of tumor cell lysis.

The fused tumor vaccine cells armed with anti-CD28 Bi-MAb were also investigated for their effectiveness in eliciting preventive and curative immunity.

For prevention experiments, groups of C57BL/6 mice were immunized subcutaneously with 1×10$^6$ fused tumor cells armed with Bi-MAbs or with control cells. After two weeks, mice were challenged with 2×10$^6$ parental tumor cells (Table VII).

For curative experiments, mice were first injected subcutaneously with parental tumor cells. After two or four weeks, mice bearing tumors were then treated by subcutaneous injection with either γ-irradiated or non-irradiated fused tumor cells armed with Bi-MAbs or with control Bi-MAb. All animals were monitored weekly and tumor size was measured using a caliper. Tumor tissues from the treated mice were routinely subjected to histopathology examination for determination of local immune responses and phenotypes of tumor infiltrating T lymphocytes as described previously

TABLE VII

| Immunization | Injecting cell No. | Challenge cell No. | Animals with tumor |
|---|---|---|---|
| BCF-hepa 1-6 | $1 \times 10^6$ | $2 \times 10^6$ | 0/5 |
|  | $1 \times 10^5$ | $2 \times 10^6$ | 2/5 |
|  | $1 \times 10^4$ | $2 \times 10^6$ | 5/5 |
| DCF-hepa 1-6 | $1 \times 10^6$ | $2 \times 10^6$ | 0/5 |
|  | $1 \times 10^5$ | $2 \times 10^6$ | 3/5 |
|  | $1 \times 10^4$ | $2 \times 10^6$ | 5/5 |
| BCF-hepa 1-6-Bi-MAb | $1 \times 10^6$ | $2 \times 10^6$ | 0/5 |
|  | $1 \times 10^5$ | $2 \times 10^6$ | 0/5 |
|  | $1 \times 10^4$ | $2 \times 10^6$ | 2/5 |
| DCF-hepa 1-6--Bi-MAb | $1 \times 10^6$ | $2 \times 10^6$ | 0/5 |
|  | $1 \times 10^5$ | $2 \times 10^6$ | 1/5 |
|  | $1 \times 10^4$ | $2 \times 10^6$ | 3/5 |
| BCF-SMCC-1 | $1 \times 10^6$ | $2 \times 10^6$ | 0/6 |
|  | $1 \times 10^5$ | $2 \times 10^6$ | 2/6 |
|  | $1 \times 10^4$ | $2 \times 10^6$ | 6/6 |
| DCF-SMCC-1 | $1 \times 10^6$ | $2 \times 10^6$ | 1/6 |
|  | $1 \times 10^5$ | $2 \times 10^6$ | 3/6 |
|  | $1 \times 10^4$ | $2 \times 10^6$ | 6/6 |
| BCF-SMCC-1-Bi-MAb | $1 \times 10^6$ | $2 \times 10^6$ | 0/6 |
|  | $1 \times 10^5$ | $2 \times 10^6$ | 0/6 |
|  | $1 \times 10^4$ | $2 \times 10^6$ | 3/6 |
| DCF-SMCC-1-Bi-MAb | $1 \times 10^6$ | $2 \times 10^6$ | 0/6 |
|  | $1 \times 10^5$ | $2 \times 10^6$ | 1/6 |
|  | $1 \times 10^4$ | $2 \times 10^6$ | 3/6 |

EXAMPLE 12

Physical Attachment of Bi-MAb to Tumor Cells before their Contact with T Cells is more Effective in Generating CTLs Than Providing Bi-MAb in Cell Culture Medium Proliferation of $CD3^+CD8^+CD25^+$ T cell population was determined and compared cytotoxicity of CTLs generated by contacting naive T cells with (a) cytokine-treated tumor cells in the presence of soluble Bi-MAb in culture medium or (b) cytokine-treated tumor cells armed with GP115×CD28 Bi-MAb without adding soluble Bi-MAb to the culture medium. Both cytokine-treated mouse and human tumor cells armed with GP115×CD28 Bi-MAb are effective in stimulating T cell proliferation and generating tumor specific CTLs in vitro. In contrast, addition of antiCD28 Bi-MAb into cell culture is much less effective in stimulating T cell proliferation and generating CTLs (Table VIII). The data clearly showed that, to create strongly immunogenic tumor cell vaccine, it is very important to arm cytokine-treated tumor cells with anti-CD28 Bi-MAb in vitro before the contact between T cells and the cellular vaccine.

Without being bound by any theory, applicant proposes that the addition of soluble Bi-MAb to cell culture is less effective because a significant proportion of the soluble Bi-MAb will bind to T cells or tumor cells but not to both. For example, a CD28 on T cell surface bound by a Bi-MAb will not be accessible to another Bi-MAb bound to the tumor cell. Such conflict between Bi-MAb bound to CD28 on one hand and Bi-MAb bound to the tumor cell on the other hand reduces the linkage between T cells and the tumor vaccine cells and thus the effectiveness of the tumor vaccine in stimulating T cell proliferation and generating CTLs.

TABLE VIII $CD3^+CD8^+CD25^+$ T cell proliferation and cytotoxicity of CTLs induced by stimulating naïve T cells in vitro with tumor vaccine cells armed with Bi-MAb or tumor vaccine cells in the presence of soluble Bi-MAb in culture medium.

| Stimulators | $CD3^+CD8^+CD25^+$ T cell ratio | Cytotoxicity(1:20) |
|---|---|---|
| CT-hepa 1-6 armed with CD28 Bi-MAb | 78% | 64% |
| CT-hepa 1-6 with CD28 Bi-MAb in medium | 37% | 26% |
| CT-hepa 1-6 armed with CD18 Bi-MAb | 14% | 9% |
| CT-hepa 1-6 with CD18 Bi-MAb in medium | 11% | 7% |
| CT-SMCC-1 armed with CD28 Bi-MAb | 68% | 71% |
| CT-SMCC-1 with CD28 Bi-MAb in medium | 31% | 29% |
| CT-SMCC-1 armed with CD18 Bi-MAb | 16% | 12% |
| CT-SMCC-1 with CD18 Bi-MAb in medium | 12% | 10% |
| CT-SL-22 armed with CD28 Bi-MAb | 54% | 47% |
| CT-SL-22 with CD28 Bi-MAb in medium | 10% | 17% |
| CT-SL-22 armed with CD18 Bi-MAb | 6% | 7% |
| CT-SL-22 with CD18 Bi-MAb in medium | 5% | 6% |

EXAMPLE 13

Adoptive Immunotherapy for Xenografted Human Hepatocellular Carcinoma in Scid Mice CTLs generated by stimulating T cells with cytokine treated hepa 1–6 cells armed with anti-CD28 Bi-MAb are effective in eliminating established tumors in syngeneic animals when administrated intravenously at a dose of $2 \times 10^7 \times 3$ in combination with I.P. injection of IL-2 (1,000 u×10). This approach is also effective in curing human xenografted tumors in immuno-deficient mouse. Three human hepatocellular carcinoma cell lines have been established from primary liver cancer tissues. All three hepatocellular carcinoma cell lines express GP115 antigens on their cell surfaces and have similar tumor formation rate to develop subcutaneous tumors when injected into nude or scid mice.

Peripheral blood T cells (PBTs) and tumor infiltrating T lymphocytes (TILs) were obtained from individual patients using a standard procedure. Briefly, T lymphocytes were obtained by stimulating these T cells with antihuman-CD3 Mab (1 ug/ml) in the presence of 100 ug/ml recombinant human IL-2. The T cells were stimulated periodically with antihuman CD3 monoclonal antibody (1 ug/ml). Irradiated peripheral blood lymphocytes from normal donors were used as feeder cells. TILs were generated from fresh tumor tissue by culturing tumor tissues in recombinant-human IL-2 medium (100 u/ml). Approximately, 55–75% of T cells and TILs were $CD3^+CD8^+CD25^+$ T cells as tested by immunofluorescent analysis. Neither T cells from peripheral blood nor TILs showed cytotoxic activity toward autologous tumor cells in vitro as assessed by a standard 4 hour $^{51}$Cr releasing assay.

The cytokine treated HCC cells armed with gp115:anti-CD28 Bi-MAb were used to to stimulate autologous PBTs or TILs for the generation of CTLs (CD8+ T cell clones) for evaluation in a human xenografted HCC system.

In preventive experiments, groups of scid mice were injected i.v. with $1 \times 10^7$ CTLs or control T cells and received, starting on day 2, i.p. injection of 1,000 u of r-IL2 every day for 7 days. Seven days after CTLs infusion, the mice were injected s.c. with 2.5×10⁶ autologous parental tumor cells. The tumor growth was monitored daily in each group (Table IXa).

In curative experiments, scid mice were first injected s.c. with parental tumor cells at a dose of 5×10⁶ cells) into right back of mouse. Two weeks later, mice with 0.5×0.5 cm tumor were injected twice i.v. with 5×10⁷ CTLs or control T cells, followed by i.p. injection of 1,000 u r-IL-2 every day for 7 days. Tumor regression and survival time were observed and recorded (Table IXb).

TABLE IX

Therapeutic efficacy of adoptive transfer CTLs generated by stimulating T cells in vitro with cytokine treated tumor cells armed with anti-CD28 monoclonal antibody.

Table IXa

| CTLs/Stimulators | CTL Dose | Tumor formation |
|---|---|---|
| CT-SL22 armed with anti-CD28 Bi-MAb | 1 × 10⁷ (×2) | 1/10 |
| CT-SL22 armed with Control Bi-MAb | 1 × 10⁷ (×2) | 9/10 |
| SL22 armed with anti-CD28 Bi-MAb | 1 × 10⁷ (×2) | 10/10 |

Table IXb

| CTLs/Stimulators | CTL Dose | Tumor regression |
|---|---|---|
| CT-SL22 armed with anti-CD28 Bi-MAb | 5 × 10⁷ (×2) | 7/10 |
| CT-SL22 armed with Control Bi-MAb | 5 × 10⁷ (×2) | 0/10 |
| SL22 armed with anti-CD28 Bi-MAb | 5 × 10⁷ (×2) | 0/10 |

EXAMPLE 14

Eradication of Tumor by Intratumor Injection of Cytokines and Bi-MAb

A method developed to avoid this toxicity is intralesional administration of immunotherapy, for instance by injection directly into the tumor or other diseased cells. Intralesional administration does not cause the toxicity seen with systemic administration of immunologic agents. Intralesional administration is also preferred when the lesion to be treated is not well vascularized, is inaccessible for biopsy, or cannot be disrupted without creating further risk to the patient. In a preferred embodiment, fine needle injection (FNI) techniques are used to provide cytokines and bridge molecules of this invention to the lesion site. For example, the techniques described and cited in Chang et al., "Phase I clinical trial of allogeneic lymphocyte culture (cytoimplant) delivered by endoscopic ultrasound (EUS)-guided fine needle injection (FNI) in patients with advanced pancreatic carcinoma" Castroenterology (1997) 112(4):A546 can be used for this invention. The injection can be assisted by imaging systems that allow physicians to visualize locations of lesions and providing the therapeutics to the right locations. The injected cytokines and Bi-MAbs are allowed to come into direct contact with tumor cells and generate CTLs targeting the tumor cells in vivo. In a preferred embodiment, the Bi-MAbs or other bridge molecules bind to an antigen present on the target diseased cells but not present on normal tissues at the disease location so as to avoid generating immune response against healthy cells. In another preferred embodiment, the Bi-MAbs or other bridge molecules bind to an antigen unique to the target diseased cells.

Cytokines and Bi-MAbs can be injected together or separately. In one embodiment, cytokines are injected into lesion locations to increase the level of one or more primary and costimulatory T cell activation molecules in target diseased cells before Bi-MAbs or other bridge molecules are injected to the same location. In another embodiment, cytokines and bridge molecules are mixed and injected to the lesion locations. Nucleic acids encoding and capable of expressing cytokines are injected to the lesion location in lieu of cytokines.

Unit dosages of cytokines and Bi-MAbs can be provided in separate containers or in the same container. In that regard, the present invention features a sterile vial or other container holding a composition comprising a unit dosage of the cytokines, Bi-MAbs, or the two in combination. Typically, the vial or container will bear a label setting forth information concerning the pharmaceutical use of the composition in treating a tumor (or other diseases) in a human, such as FDA approval for use of the composition in the treatment of a human having one or more of the tumors (or other diseases) against which the method of treatment of the invention is effective as described herein.

Other molecules capable of increasing the level of one or more primary and costimulatory T cell activation molecules in target diseased cells may also be provided in lieu of or in addition to cytokines, e.g., MHC and B7.

Human patients with localized and surgically accessible tumors are logical candidates for intralesional immunotherapy. Both primary tumors and secondary or metastatic tumors can be treated in this way. Examples of tumors that can be treated by the method of this invention include the following:

Brain tumors, such as glioma, astrocytoma, oligodendroglioma, ependymoma, medulloblastomas, and PNET (Primitive Neural Ectodermal Tumor);

Pancreatic tumors, such as pancreatic ductal adenocarcinomas;

Lung tumors, such as small and large cell adenocarcinomas, squamous cell carcinoma, and bronchoalveolarcarcinoma;

Colon tumors, such as epithelial adenocarcinoma, and liver metastases of these tumors;

Liver tumors, such as hepatoma, and cholangiocarcinoma;

Breast tumors, such as ductal and lobular adenocarcinoma;

Gynecologic tumors, such as squamous and adenocarcinoma of the uterine cervix, and uterine and ovarian epithelial adenocarcinoma;

Prostate tumors, such as prostatic adenocarcinoma;

Bladder tumors, such as transitional, squamous cell carcinoma;

Skin tumors, such as malignant melanoma; and

Soft tissue tumors, such as soft tissue sarcoma and leiomyosarcoma.

The results above have shown that effective tumor vaccines can be generated by treatment of tumor cells with a combination of cytokine and pre-incubated with an anti-CD28 Bi-MAb. This two-step process can be effectively modified by intratumor injection of a combination of cytokine and an anti-CD28 Mab (or other bridge molecules) which has a binding site to recognize antigens specific expressed on mouse cancer cells such as gp210, gp115 and gp55. The efficacy of intratumor injection of cytokine and Bi-MAb in induction of anti-tumor immunity was first determined in syngeneic hepa 1–6 and SMCC-1 mouse tumor model.

Groups of C57 mice were subcutaneously injected with 1×10⁶ hepa 1–6-tumor cells. Two weeks after tumor inoculation, mice with grossly identifiable tumors were injected intratumorally with a combination of 200 u IFN-γ and 200 u TNF-A daily×3 and followed by an intratumor injection of Bi-MAb at a dose of 500 ug at the 3rd day after last injection of cytokines. Mice taken intratumor injection of both cytokines and Bi-MAb showed significant tumor regression and extended survival time. This experiment supports that intratumor injection of cytokines and Bi-MAb is a way of generating tumor vaccines in vivo.

TABLE X

| Tumor models | Cytokines | Bi-MAb | Tumor regression | |
|---|---|---|---|---|
| Hepa 1-6 | IFN-γ + TNF-α | | 0/6 | 0/4 |
| Hepa 1-6 | | GP115xCD28 | 0/6 | 0/4 |
| Hepa 1-6 | IFN-γ + TNF-α | GP115xCD28 | 4/6 | 3/4 |
| SMCC-1 | IFN-γ + TNF-α | | 0/5 | 0/5 |
| SMCC-1 | | GP115xCD28 | 0/5 | 0/5 |
| SMCC-1 | IFN-γ + TNF-α | GP115xCD28 | 3/5 | 4/5 |

EXAMPLE 15

Intra-spenic Administration of Vaccines

It is likely that the initial contact between T cells and vaccine occurs within peripheral lymph organs such as spleen or lymph nodes rather then at the site of primary injection. Injection to a peripheral tissue site (such as skin) or intravenously may lead to a substantial loss of DCs during migration into spleen or lymph node. Therefore, direct injection into a lymphoid organ may be desirable. Our data showed that a single intrasplenic injection of $2.5 \times 10^4$ cytokine treated hepa 1–6 cells armed with Bi-MAb was sufficient to elicit anti-tumor immune response against parental tumor cell challenge. Xenografted human melanoma and hepatoma cancer models can be used to determine the effectiveness of this approach and the minimum number of cytokine treated tumor cells armed with Bi-MAb required for effective vaccination. Mice having reconstituted human immune system will be first inoculated subcutaneously with $2 \times 10^6$ human melanoma or hepatoma cancer cell lines. After either two or four weeks, mice bearing tumor will be injected intrasplenically with $1 \times 10^3$, $1 \times 10^4$, $2 \times 10^4$, $5 \times 10^4$ or $1 \times 10^6$ cytokine treated autologous tumor cells armed with Bi-MAb or control Bi-MAb. Vaccine cells can be directly injected into spleen using a #31 needle via a surgical approach through the back. The clinical application of this approach can be extended to intra-lymph node injection in human.

EXAMPLE 16

Human Clinical Data
Immunotherapy With Cancer Vaccine

The above data show that tumor cells treated with a combination of cytokines and armed in vitro with Bi-MAb became more immunogenic and can cure established hepatoma and colon carcinoma in both mouse and rat models. To evaluate clinical effectiveness of the cellular vaccines on treatment of human hepatocellular carcinoma (HCC) and colon cancer, applicant generated human cellular vaccines using this two-step process and treated 13 HCC patients and 5 colon cancer patients.

In HCC patients, stages were II in 3, III in 7, and IV in 3 and in colon cancer patients, all had distant metastasis. All treated patients had a pathological diagnosis.

Each patient received subcutaneous injection of $1-1.5 \times 10^7$ tumor vaccines twice within a two week period. Fifteen patients experienced a 37.8–38.6° C. fever after the second injection that continued for 8 to 15 hours. No other toxic and allergic reactions were observed. DTH reactions to autologous tumor cells were significantly increased in 11 of 18 patients. Two patients had complete regression of metastatic lesions and four patients had partial regression of metastasis after treatment. Primary tumor regression >30% in size occurred in four HCC patients. In two patients with significantly tumor regression, tumors became operable and were successfully excised. Histopathology demonstrated marked necrosis and abundant lymphocyte infiltration in tumor tissues.

Combination Immunotherapy with Cancer Vaccine and Adoptive Transfer of Tumor Specific CTLs 11 hepatocellular carcinoma (HCC) and 5 gastric cancer (GC) patients were treated by the combined immunotherapy. In HCC patients, stages were III in 5 and stage IV in 6. All GC patients had recurrent metastasis. Each patient was injected s.c. with $1-1.5 \times 10^7$ tumor vaccines twice within a two-week period followed by infusion of $1.7-2.1 \times 10^9$ TS-CTLs. All patients experienced 37.8–38.8° C. fever after the second injection of vaccine cells that continued for 8 to 20 hours. No other toxic and allergic reactions were observed.

DTH reactions to autologous tumor cells were observed in 13 of 17 patients. Proliferation of T cells from the treated patients (14 cases) was significantly increased. Four patients had a significant regression of metastatic lesions and three patients had a partial regression of metastasis. Ascites completely disappeared in two GC patients after treatment. Abundant lymphocyte infiltration and necrosis were demonstrated in tumor tissues from six treated patients. The results suggest that the combination of cellular vaccines and adoptive TS-CTLs immunotherapy provide an improved immunotherapy strategy for treating human cancers.

Protocols

Cytokines treatment of the tumor cells: Cells were plated into 24-well tissue culture plates at concentration of $2 \times 10^6$ cells/ml in RPMI-1640 complete medium with IFN-γ (100 U/ml) and TNF-cc (50 U/ml) added freshly. Incubate the plate in 5% $CO_2$, 37° C. incubator for 48 h.

Preparation of cellular tumor vaccines in vitro: After treated for 48 h in vitro with a combination of IFN-γ and TNF-α, cells were then washed with PBS (pH 7.4)×3 at room temperature and incubated with anti-CD28 Bi-MAb at a concentration of 50 μg/ml on ice for 45 min. After being washed, cells were subjected to an additional incubation with an equal volume of 30% polyethylene (PEG) in RPMI-1640 at 4° C. for 30 min as previously reported (Huang, et al., (1994) Science 264:961–5). Finally, the cells were again washed with PBS×3 and suspended in a final concentration of $1-2 \times 10^7$/ml PBS.

Generation of CTLs and cytotoxicity assays: To stimulate tumor-specific CTL responses purified peripheral blood T cells or TILs were primed with y-irradiated (5000 rad) cytokine-treated tumor cells armed with Bi-Mab for 9 days in complete RPMI-1640 medium, supplemented with 20 units/ml IL-2. The cytotoxic activity of in vitro stimulated T cells was determined using the $^{51}Cr$ release assay.

TABLE XI

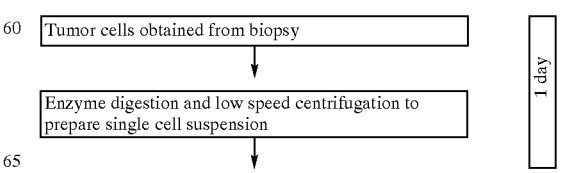

TABLE XI-continued

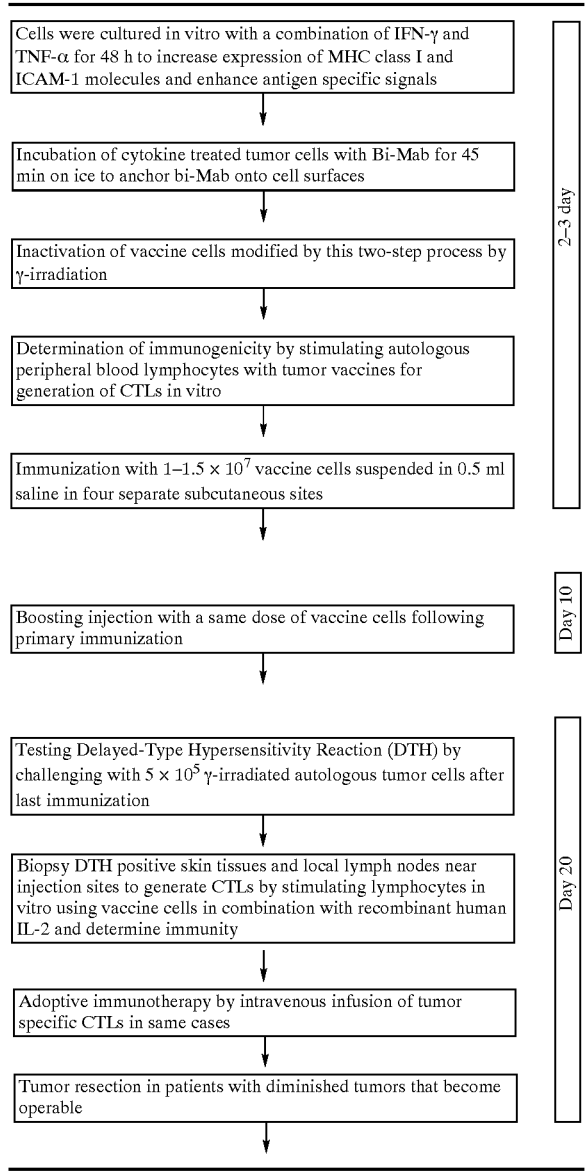

EXAMPLE 17

Generation of Human Melanoma Vaccines

Eight human melanoma cell lines have been established from primary melanoma tissues of patients. These melanoma cell lines express gp115 antigens on cell surfaces and develop subcutaneous tumors when injected into nude or SCID mice. Neither peripheral blood T cells (PBTs) nor tumor infiltrating lymphocytes (TILs) obtained from these patients showed any cytotoxic activity toward autologous tumor cells in vitro as assessed by a standard 4 h $^{51}$Cr release assay.

The cytokine treated human melanoma cells armed with gp115:anti-CD28 Bi-MAb will be tested for their ability to stimulate autologous PBTs or TILs for the generation of CTLs. CD8$^+$ T cell clones will be established by the stimulation of cytokine treated human melanoma cells armed with gp115:anti-CD28 Bi-MAb. The cytotoxic specificities of the CD8$^+$ T cell clones toward various human tumor cells will be evaluated in a human xenografted melanoma system.

Before human testing, it will be determined whether adoptive transfer of these CD8$^+$ T cell clones into SCID mice bearing autologous human melanomas can inhibit tumor growth and cure the established tumors. For example, SCID mice, in groups of five, will be injected subcutaneously with human melanoma cells in the right flank of mice ($5\times10^6$/each). Two weeks after tumor inoculation, mice with grossly identifiable tumors will be injected intravenously with $2\times10^7$ CD8$^+$ T cells and followed by a daily administration of 1,000 u recombinant-human IL-2×10. Tumor regression and survival time will be monitored. If tumor regression occurs, some of the mice will be sacrificed and tumor tissues will be examined by histopathological approaches. Different numbers of CD8$^+$ T cell clones will be adoptively transferred to allow the comparison of the effectiveness of the T cell clones in eradicating the established tumors.

The present invention is not to be limited in scope by the embodiments disclosed herein, which are intended as single illustrations of individual aspects of the invention, and any which are functionally equivalent are within the scope of the invention. Various modifications of the invention, in addition to those shown and described herein, will become apparent to those skilled in the art from the foregoing description, and are similarly intended to fall within the scope of the invention. For example, Guo et al., *Nature Medicine*, vol. 4:451–455, (April, 1997) provide examples and references.

All publications referenced are incorporated by reference herein, including drawings, nucleic acid sequences and amino acid sequences listed in each publications. All the compounds disclosed and referred to in the publications mentioned above are incorporated by reference herein, including those compounds disclosed and referred to in articles cited by the publications mentioned above.

Other embodiments of this invention are disclosed in the following claims.

What is claimed is:

1. A method of preparing an immunogenic composition, comprising the steps of:
   (a) providing an autologous target tumor or pathogen infected cell;
   (b) treating the tumor or pathogen infected cell with IFN-γ and/or TNF-α to increase concentration of a primary T cell activation molecule or a costimulatory T cell activation molecule in the target tumor or pathogen infected cell;
   (c) providing a bispecific monoclonal antibody including one or more binding sites for one or more costimulatory molecules on a surface of one or more T cells of a patient mammal, wherein the bispecific antibody is a CD28:gp55 bispecific monoclonal antibody;
   (d) attaching the bispecific monoclonal antibody to the target tumor or pathogen infected cell; and
   (e) collecting a pharmaceutically effective amount of the target tumor or pathogen infected cell with the attached bispecific monoclonal antibody.

2. The method of claim 1, wherein an autologous target tumor cell is provided.

3. The method of claim 2, wherein the tumor cell is selected from the group consisting of a hepatocellular carcinoma cell, a lymphoma cell, a colon carcinoma cell and a gastric cancer cell.

4. The method of claim 1, wherein the T cell is selected from the group consisting of a CD3+, a CD8+ and a CD2S+ T cell.

5. The method of claim 1, wherein the bispecific monoclonal antibody includes two or more binding sites for two or more costimulatory molecules on a surface of one or more T veils of a patient mammal.

6. The method of claim 1, wherein the autologous target tumor or pathogen infected cell is a human cell.

7. The method of claim 1, further comprising removing the bispecific monoclonal antibody not attached to the target tumor or pathogen infected cell before step (e).

8. A method of preparing an immunogenic composition, comprising the steps of:

(a) providing an autologous target tumor cell;
(b) treating the tumor cell with IFN-γ and/or TNF-α to increase concentration of CD28 in the target tumor cell;
(c) providing a CD28:gp55 bispecific monoclonal antibody;
(d) attaching the CD28:gp55 bispecific monoclonal antibody to the target tumor cell; and
(e) collecting a pharmaceutically effective amount of the target tumor cell with the attached CD2S:gp55 bispecific monoclonal antibody.

* * * * *